United States Patent
Ku et al.

(10) Patent No.: US 11,026,707 B2
(45) Date of Patent: Jun. 8, 2021

(54) SHOCK WAVE DEVICE WITH POLARITY SWITCHING

(71) Applicant: Shockwave Medical, Inc., Santa Clara, CA (US)

(72) Inventors: Vincent Wenchung Ku, Palo Alto, CA (US); Camilo Perez Saaibi, Fremont, CA (US)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 168 days.

(21) Appl. No.: 16/261,391

(22) Filed: Jan. 29, 2019

(65) Prior Publication Data
US 2019/0175198 A1    Jun. 13, 2019

Related U.S. Application Data

(63) Continuation of application No. 15/138,147, filed on Apr. 25, 2016, now Pat. No. 10,226,265.

(51) Int. Cl.
*A61B 17/22* (2006.01)
*A61B 17/00* (2006.01)

(52) U.S. Cl.
CPC .... *A61B 17/2202* (2013.01); *A61B 17/22022* (2013.01); *A61B 17/22029* (2013.01);
(Continued)

(58) Field of Classification Search
CPC .......... A61B 17/2202; A61B 17/22022; A61B 17/22029; A61B 17/00172;
(Continued)

(56) References Cited

U.S. PATENT DOCUMENTS 3,413,976 A   12/1968  Roze
3,785,382 A   1/1974   Schmidt et al.
(Continued)

FOREIGN PATENT DOCUMENTS

CN   1269708 A    10/2000
CN   102057422 A   5/2011
(Continued)

OTHER PUBLICATIONS

Extended European Search Report received for European Patent Application No. 20150366.1, dated Feb. 6, 2020, 11 pages.
(Continued)

*Primary Examiner* — Kathleen S Holwerda
*Assistant Examiner* — Brooke Labranche
(74) *Attorney, Agent, or Firm* — Morrison & Foerster LLP

(57) ABSTRACT

Described here are devices and methods for forming shock waves. The devices may comprise an axially extending elongate member. A first electrode pair may comprise a first electrode and a second electrode. The first electrode pair may be provided on the elongate member and positioned within a conductive fluid. A controller may be coupled to the first electrode pair. The controller may be configured to deliver a series of individual pulses to the first electrode pair, where each pulse creates a shock wave. The controller may cause current to flow through the electrode pair in a first direction for some of the pulses in the series and in a second direction opposite the first direction for the remaining pulses in the series.

9 Claims, 11 Drawing Sheets

(52) U.S. Cl.
CPC .......... *A61B 2017/0019* (2013.01); *A61B 2017/00172* (2013.01); *A61B 2017/00411* (2013.01); *A61B 2017/22001* (2013.01); *A61B 2017/22021* (2013.01); *A61B 2017/22025* (2013.01); *A61B 2017/22062* (2013.01); *A61B 2017/22068* (2013.01); *A61B 2017/22097* (2013.01); *A61B 2017/22098* (2013.01)

(58) Field of Classification Search
CPC .......... A61B 17/0019; A61B 17/00411; A61B 17/22001; A61B 17/22021; A61B 17/22025; A61B 17/22062; A61B 17/22068; A61B 17/22097; A61B 17/22098
See application file for complete search history.

(56) References Cited

U.S. PATENT DOCUMENTS

| | | | |
|---|---|---|---|
| 3,902,499 A | 9/1975 | Shene | |
| 4,027,674 A | 6/1977 | Tessler et al. | |
| 4,662,126 A | 5/1987 | Malcolm | |
| 4,671,254 A | 6/1987 | Fair | |
| 4,685,458 A | 8/1987 | Leckrone | |
| 4,799,482 A | 1/1989 | Takayama | |
| 4,809,682 A | 3/1989 | Forssmann et al. | |
| 4,813,418 A | 3/1989 | Harris | |
| 4,900,303 A | 2/1990 | Lemelson | |
| 5,009,232 A | 4/1991 | Hassler et al. | |
| 5,057,103 A | 10/1991 | Davis | |
| 5,057,106 A | 10/1991 | Kasevich et al. | |
| 5,078,717 A | 1/1992 | Parins et al. | |
| 5,103,804 A | 4/1992 | Abele et al. | |
| 5,152,767 A | 10/1992 | Sypal et al. | |
| 5,152,768 A | 10/1992 | Bhatia | |
| 5,176,675 A | 1/1993 | Watson et al. | |
| 5,245,988 A | 9/1993 | Einars et al. | |
| 5,246,447 A | 9/1993 | Rosen et al. | |
| 5,281,231 A | 1/1994 | Rosen et al. | |
| 5,321,715 A | 6/1994 | Trost | |
| 5,324,255 A | 6/1994 | Passafaro et al. | |
| 5,336,234 A | 8/1994 | Vigil et al. | |
| 5,362,309 A | 11/1994 | Carter | |
| 5,364,393 A | 11/1994 | Auth et al. | |
| 5,368,591 A | 11/1994 | Lennox et al. | |
| 5,395,335 A | 3/1995 | Jang | |
| 5,417,208 A | 5/1995 | Winkler | |
| 5,425,735 A | 6/1995 | Rosen et al. | |
| 5,472,406 A | 12/1995 | De et al. | |
| 5,540,682 A | 7/1996 | Gardner et al. | |
| 5,582,578 A | 12/1996 | Zhong et al. | |
| 5,603,731 A | 2/1997 | Whitney | |
| 5,609,606 A | 3/1997 | O'Boyle | |
| 5,662,590 A | 9/1997 | De et al. | |
| 5,931,805 A | 8/1999 | Brisken | |
| 6,007,530 A | 12/1999 | Dornhofer et al. | |
| 6,033,371 A | 3/2000 | Torre et al. | |
| 6,083,232 A | 7/2000 | Cox | |
| 6,186,963 B1 | 2/2001 | Schwarze et al. | |
| 6,210,408 B1 | 4/2001 | Chandrasekaran et al. | |
| 6,217,531 B1 | 4/2001 | Reitmajer | |
| 6,277,138 B1 | 8/2001 | Levinson et al. | |
| 6,287,272 B1 | 9/2001 | Brisken et al. | |
| 6,352,535 B1 | 3/2002 | Lewis et al. | |
| 6,367,203 B1 | 4/2002 | Graham et al. | |
| 6,371,971 B1 | 4/2002 | Tsugita et al. | |
| 6,398,792 B1 | 6/2002 | O"Connor | |
| 6,406,486 B1 | 6/2002 | De La Torre et al. | |
| 6,514,203 B2 | 2/2003 | Bukshpan | |
| 6,524,251 B2 | 2/2003 | Rabiner et al. | |
| 6,589,253 B1 | 7/2003 | Cornish et al. | |
| 6,607,003 B1 | 8/2003 | Wilson | |
| 6,638,246 B1 | 10/2003 | Naimark et al. | |
| 6,652,547 B2 | 11/2003 | Rabiner et al. | |
| 6,736,784 B1 | 5/2004 | Menne et al. | |
| 6,740,081 B2 | 5/2004 | Hilal | |
| 6,755,821 B1 | 6/2004 | Fry | |
| 6,989,009 B2 | 1/2006 | Lafontaine | |
| 7,241,295 B2 | 7/2007 | Maguire | |
| 7,505,812 B1 | 3/2009 | Eggers et al. | |
| 7,569,032 B2 | 8/2009 | Naimark et al. | |
| 7,873,404 B1 | 1/2011 | Patton | |
| 8,556,813 B2 | 10/2013 | Cioanta et al. | |
| 8,574,247 B2 | 11/2013 | Adams et al. | |
| 8,712,533 B2 | 4/2014 | Alataris et al. | |
| 8,728,091 B2 | 5/2014 | Hakala et al. | |
| 8,747,416 B2 | 6/2014 | Hakala et al. | |
| 8,888,788 B2 | 11/2014 | Hakala et al. | |
| 8,956,371 B2 | 2/2015 | Hawkins et al. | |
| 9,005,216 B2 | 4/2015 | Hakala et al. | |
| 9,011,463 B2 * | 4/2015 | Adams ............... | A61B 18/1492 606/128 |
| 9,044,618 B2 | 6/2015 | Hawkins et al. | |
| 9,072,534 B2 | 7/2015 | Adams et al. | |
| 9,138,249 B2 | 9/2015 | Adams et al. | |
| 9,180,280 B2 | 11/2015 | Hawkins et al. | |
| 9,220,521 B2 | 12/2015 | Hawkins et al. | |
| 9,237,984 B2 | 1/2016 | Hawkins et al. | |
| 9,333,000 B2 | 5/2016 | Hakala et al. | |
| 10,226,265 B2 * | 3/2019 | Ku .................. | A61B 17/22029 |
| 2001/0044596 A1 | 11/2001 | Jaafar | |
| 2002/0045890 A1 | 4/2002 | Celliers et al. | |
| 2002/0177889 A1 | 11/2002 | Brisken et al. | |
| 2003/0004434 A1 | 1/2003 | Greco et al. | |
| 2003/0176873 A1 | 9/2003 | Chernenko et al. | |
| 2003/0229370 A1 | 12/2003 | Miller | |
| 2004/0044308 A1 | 3/2004 | Naimark et al. | |
| 2004/0097963 A1 | 5/2004 | Seddon | |
| 2004/0097996 A1 | 5/2004 | Rabiner et al. | |
| 2004/0162508 A1 | 8/2004 | Uebelacker | |
| 2004/0254570 A1 | 12/2004 | Hadjicostis et al. | |
| 2005/0015953 A1 | 1/2005 | Keidar | |
| 2005/0021013 A1 | 1/2005 | Visuri et al. | |
| 2005/0113722 A1 | 5/2005 | Schultheiss | |
| 2005/0113822 A1 | 5/2005 | Fuimaono et al. | |
| 2005/0228372 A1 | 10/2005 | Truckai et al. | |
| 2005/0251131 A1 | 11/2005 | Lesh | |
| 2006/0004286 A1 | 1/2006 | Chang et al. | |
| 2006/0184076 A1 | 8/2006 | Gill et al. | |
| 2006/0190022 A1 | 8/2006 | Beyar et al. | |
| 2007/0016112 A1 | 1/2007 | Schultheiss et al. | |
| 2007/0088380 A1 | 4/2007 | Hirszowicz et al. | |
| 2007/0239082 A1 | 10/2007 | Schultheiss et al. | |
| 2007/0239253 A1 | 10/2007 | Jagger et al. | |
| 2007/0244423 A1 | 10/2007 | Zumeris et al. | |
| 2007/0255270 A1 | 11/2007 | Carney | |
| 2007/0282301 A1 | 12/2007 | Segalescu et al. | |
| 2008/0097251 A1 | 4/2008 | Babaev | |
| 2008/0188913 A1 | 8/2008 | Stone et al. | |
| 2009/0041833 A1 | 2/2009 | Bettinger et al. | |
| 2009/0247945 A1 | 10/2009 | Levit et al. | |
| 2009/0254114 A1 | 10/2009 | Hirszowicz et al. | |
| 2009/0312768 A1 | 12/2009 | Hawkins et al. | |
| 2010/0016862 A1 | 1/2010 | Hawkins et al. | |
| 2010/0036294 A1 | 2/2010 | Mantell et al. | |
| 2010/0114020 A1 | 5/2010 | Hawkins et al. | |
| 2010/0114065 A1 | 5/2010 | Hawkins et al. | |
| 2010/0121322 A1 | 5/2010 | Swanson | |
| 2010/0305565 A1 | 12/2010 | Truckai et al. | |
| 2011/0034832 A1 | 2/2011 | Cioanta et al. | |
| 2011/0118634 A1 | 5/2011 | Golan | |
| 2011/0166570 A1 | 7/2011 | Hawkins et al. | |
| 2011/0208185 A1 | 8/2011 | Diamant et al. | |
| 2011/0257523 A1 | 10/2011 | Hastings et al. | |
| 2011/0295227 A1 | 12/2011 | Hawkins et al. | |
| 2012/0071889 A1 | 3/2012 | Mantell et al. | |
| 2012/0095461 A1 | 4/2012 | Herscher et al. | |
| 2012/0116289 A1 | 5/2012 | Hawkins et al. | |
| 2012/0203255 A1 | 8/2012 | Hawkins et al. | |
| 2012/0221013 A1 | 8/2012 | Hawkins et al. | |
| 2013/0030431 A1 | 1/2013 | Adams | |
| 2013/0030447 A1 | 1/2013 | Adams | |
| 2013/0150874 A1 | 6/2013 | Kassab | |

(56) References Cited

U.S. PATENT DOCUMENTS

| | | |
|---|---|---|
| 2014/0005576 A1 | 1/2014 | Adams et al. |
| 2014/0031813 A1 | 1/2014 | Tellio et al. |
| 2014/0039513 A1 | 2/2014 | Hakala et al. |
| 2014/0046229 A1 | 2/2014 | Hawkins et al. |
| 2014/0046353 A1 | 2/2014 | Adams |
| 2014/0052145 A1 | 2/2014 | Adams et al. |
| 2014/0052147 A1 | 2/2014 | Hakala et al. |
| 2014/0074111 A1 | 3/2014 | Hakala et al. |
| 2014/0074113 A1 | 3/2014 | Hakala et al. |
| 2014/0243820 A1 | 8/2014 | Adams et al. |
| 2014/0243847 A1 | 8/2014 | Hakala et al. |
| 2014/0288570 A1 | 9/2014 | Adams |
| 2014/0376269 A1* | 12/2014 | Johnson ............ A61B 18/1206 363/17 |
| 2015/0039002 A1 | 2/2015 | Hawkins |
| 2015/0073430 A1 | 3/2015 | Hakala et al. |
| 2015/0238208 A1 | 8/2015 | Adams et al. |
| 2015/0320432 A1 | 11/2015 | Adams |
| 2016/0151081 A1 | 6/2016 | Adams et al. |
| 2016/0183957 A1 | 6/2016 | Hakala et al. |
| 2016/0324534 A1 | 11/2016 | Hawkins et al. |

FOREIGN PATENT DOCUMENTS

| | | |
|---|---|---|
| CN | 102271748 A | 12/2011 |
| CN | 202113127 U | 1/2012 |
| CN | 102765785 A | 11/2012 |
| DE | 3038445 A1 | 5/1982 |
| EP | 0082508 A1 | 6/1983 |
| EP | 0442199 A2 | 8/1991 |
| EP | 0571306 A1 | 11/1993 |
| JP | 62-275446 A | 11/1987 |
| JP | 6-125915 A | 5/1994 |
| JP | 7-47135 A | 2/1995 |
| JP | H1066734 A | 3/1998 |
| JP | 10-99444 A | 4/1998 |
| JP | 10-513379 A | 12/1998 |
| JP | 2002-538932 A | 11/2002 |
| JP | 2004-81374 A | 3/2004 |
| JP | 2005-95410 A | 4/2005 |
| JP | 2005-515825 A | 6/2005 |
| JP | 2006-516465 A | 7/2006 |
| JP | 2007-532182 A | 11/2007 |
| JP | 2008-506447 A | 3/2008 |
| JP | 2015-528327 A | 9/2015 |
| WO | 1996/24297 A1 | 8/1996 |
| WO | 1999/02096 A1 | 1/1999 |
| WO | 2004/069072 A2 | 8/2004 |
| WO | 2005/099594 A1 | 10/2005 |
| WO | 2006/127158 A2 | 11/2006 |
| WO | 2007/149905 A2 | 12/2007 |
| WO | 2009/121017 A1 | 10/2009 |
| WO | 2009/126544 A1 | 10/2009 |
| WO | 2009/152352 A2 | 12/2009 |
| WO | 2010/014515 A2 | 2/2010 |
| WO | 2011/143468 A2 | 11/2011 |
| WO | 2012/025833 A2 | 3/2012 |
| WO | 2013/059735 A1 | 4/2013 |
| WO | WO-2017189068 A1 | 11/2017 |

OTHER PUBLICATIONS

Advisory Action received for U.S. Appl. No. 13/615,107, dated Nov. 6, 2015, 3 pages.
Advisory Action received for U.S. Appl. No. 12/482,995, dated Jun. 2, 2014, 3 pages.
Advisory Action received for U.S. Appl. No. 12/482,995, dated Sep. 29, 2011, 2 pages.
Advisory Action received for U.S. Appl. No. 12/581,295, dated Jul. 3, 2014, 3 pages.
Advisory Action received for U.S. Appl. No. 13/049,199, dated Jun. 7, 2012, 3 pages.
Advisory Action received for U.S. Appl. No. 13/267,383, dated Jan. 6, 2014, 4 pages.
Advisory Action received for U.S. Appl. No. 15/138,147, dated Jul. 10, 2018, 3 pages.
Cleveland et al., "The Physics of Shock Wave Lithotripsy", Extracorporeal Shock Wave Lithotripsy Part IV, Chapter 38, 2012, pp. 317-332.
Connors et al., "Renal Nerves Mediate Changes in Contralateral Renal Blood Flow after Extracorporeal Shockwave Lithotripsy", Nephron Physiology, vol. 95, 2003, pp. 67-75.
Decision to Grant received for European Patent Application No. 13756766.5, dated May 27, 2016, 2 pages.
Decision to Grant received for Japanese Patent Application No. 2011-513694, dated Oct. 7, 2014, 3 pages.
Extended European Search Report (includes Supplementary European Search Report and Search Opinion) received for European Patent Application No. 09763640.1, dated Oct. 10, 2013, 5 pages.
Extended European Search Report received for European Patent Application No. 13827971.6, dated Apr. 12, 2016, 8 pages.
Final Office Action received for U.S. Appl. No. 14/271,342 dated Feb. 27, 2015, 7 pages.
Final Office Action received for U.S. Appl. No. 12/482,995, dated Feb. 20, 2014, 11 pages.
Final Office Action received for U.S. Appl. No. 12/581,295, dated Jun. 5, 2014, 14 pages.
Final Office Action received for U.S. Appl. No. 13/049,199 dated Aug. 11, 2014, 8 pages.
Final Office Action received for U.S. Appl. No. 13/267,383, dated May 28, 2015, 12 pages.
Final Office Action received for U.S. Appl. No. 13/267,383, dated Oct. 25, 2013, 8 pages.
Final Office Action received for U.S. Appl. No. 13/534,658, dated Aug. 23, 2016, 11 pages.
Final Office Action received for U.S. Appl. No. 13/615,107 dated Sep. 1, 2015, 9 pages.
Final Office Action received for U.S. Appl. No. 13/646,570, dated Dec. 23, 2014, 10 pages.
Final Office Action received for U.S. Appl. No. 14/229,735, dated Aug. 27, 2015, 7 pages.
Final Office Action received for U.S. Appl. No. 15/138,147, dated Apr. 25, 2018, 11 pages.
Gambihler et al., "Permeabilization of the Plasma Membrane of LI210 Mouse Leukemia Cells Using Lithotripter Shock Waves", the Journal of Membrane Biology, vol. 141, 1994, pp. 267-275.
Grassi et al., "Novel Antihypertensive Therapies: Renal Sympathetic Nerve Ablation and Carotid Baroreceptor Stimulation", Curr Hypertens Rep, vol. 14, 2012, pp. 567-572.
Hawkins et al., U.S. Appl. No. 14/940,029, filed Nov. 12, 2015, titled "Shock Wave Valvuloplasty Device and Methods".
Intention to Grant received for European Patent Application No. 13756766.5, dated Jan. 8, 2016, 5 pages.
International Preliminary Report on Patentability received for PCT Patent Application No. PCT/US2009/047070, dated Dec. 23, 2010, 7 pages.
International Preliminary Report on Patentability received for PCT Patent Application No. PCT/US2011/047070, dated Feb. 21, 2013, 7 pages.
International Preliminary Report on Patentability received for PCT Patent Application No. PCT/US2012/023172, dated Aug. 15, 2013, 6 pages.
International Preliminary Report on Patentability received for PCT Patent Application No. PCT/US2013/031805, dated Feb. 19, 2015, 11 pages.
International Preliminary Report on Patentability received for PCT Patent Application No. PCT/US2013/039987 dated Nov. 20, 2014, 11 pages.
International Preliminary Report on Patentability received for PCT Patent Application No. PCT/US2013/048277 dated Jan. 8, 2015, 9 pages.
International Preliminary Report on Patentability received for PCT Patent Application No. PCT/US2013/055431, dated Feb. 26, 2015, 7 pages.

(56) References Cited

OTHER PUBLICATIONS

International Preliminary Report on Patentability received for PCT Patent Application No. PCT/US2013/059533 dated Mar. 26, 2015, 10 pages.
International Search Report and Written Opinion received for PCT Patent Application No. PCT/US2017/016066, dated Mar. 17, 2017, 16 pages.
International Search Report and Written Opinion received for PCT Patent Application No. PCT/US2013/031805 dated May 20, 2013, 13 pages.
International Search Report and Written Opinion received for PCT Patent Application No. PCT/US2013/039987, dated Sep. 23, 2013, 15 pages.
International Search Report and Written Opinion received for PCT Patent Application No. PCT/US2013/048277, dated Oct. 2, 2013, 14 pages.
International Search Report and Written Opinion received for PCT Patent Application No. PCT/US2013/055431, dated Nov. 12, 2013, 9 pages.
International Search Report and Written Opinion received for PCT Patent Application No. PCT/US2013/059533, dated Nov. 7, 2013, 14 pages.
International Search Report and Written Opinion received for PCT Patent Application No. PCT/US2015/029088 dated Jul. 16, 2015, 13 pages.
International Search Report received for PCT Patent Application No. PCT/US2009/047070, dated Jan. 19, 2010, 4 pages.
International Search Report received for PCT Patent Application No. PCT/US2012/023172, dated Sep. 28, 2012, 3 pages.
International Written Opinion received for PCT Patent Application No. PCT/US2011/047070, dated May 1, 2012, 5 pages.
International Written Opinion received for PCT Patent Application No. PCT/US2012/023172, dated Sep. 28, 2012, 4 pages.
International Written Opinion received for PCT Patent Application No. PCT/US2009/047070, dated Jan. 19, 2010, 5 pages.
Kodama et al., "Shock Wave-Mediated Molecular Delivery into Cells", Biochimica et Biophysica Acta, vol. 1542, 2002, pp. 186-194.
Lauer et al., "Shock Wave Permeabilization as a New Gene Transfer Method", Gene Therapy, vol. 4, 1997, pp. 710-715.
Non-Final Office Action received for U.S. Appl. No. 12/482,995, dated Aug. 13, 2014, 10 pages.
Non-Final Office Action received for U.S. Appl. No. 12/482,995, dated Jul. 12, 2013, 11 pages.
Non-Final Office Action received for U.S. Appl. No. 13/465,264, dated Oct. 29, 2014, 13 pages.
Non-Final Office Action received for U.S. Appl. No. 13/646,570, dated Oct. 29, 2014, 10 pages.
Non-Final Office Action received for U.S. Appl. No. 14/079,463, dated Mar. 4, 2014, 9 pages.
Non-Final Office Action received for U.S. Appl. No. 13/534,658, dated Mar. 11, 2016, 12 pages.
Non-Final Office Action received for U.S. Appl. No. 14/218,858, dated Mar. 30, 2016, 13 pages.
Non-Final Office Action received for U.S. Appl. No. 14/515,130, dated Jan. 14, 2016, 16 pages.
Non-Final Office Action received for U.S. Appl. No. 12/501,619, dated Jan. 28, 2014, 10 pages.
Non-Final Office Action received for U.S. Appl. No. 12/581,295, dated Jan. 15, 2015, 14 pages.
Non-Final Office Action received for U.S. Appl. No. 12/581,295, dated Mar. 10, 2014, 11 pages.
Non-Final Office Action received for U.S. Appl. No. 13/049,199, dated Feb. 4, 2014, 8 pages.
Non-Final Office Action received for U.S. Appl. No. 13/267,383, dated Feb. 25, 2015, 9 pages.
Non-Final Office Action received for U.S. Appl. No. 13/465,264, dated Dec. 23, 2014, 13 pages.
Non-Final Office Action received for U.S. Appl. No. 13/615,107, dated Apr. 24, 2015, 9 pages.
Non-Final Office Action received for U.S. Appl. No. 13/646,583, dated Oct. 31, 2014, 8 pages.
Non-Final Office Action received for U.S. Appl. No. 14/061,554, dated Mar. 12, 2014, 14 pages.
Non-Final Office Action received for U.S. Appl. No. 14/271,276, dated Aug. 4, 2014, 7 pages.
Non-Final Office Action received for U.S. Appl. No. 14/271,342, dated Sep. 2, 2014, 6 pages.
Non-Final Office Action received for U.S. Appl. No. 14/273,063, dated Jun. 3, 2016, 9 pages.
Non-Final Office Action received for U.S. Appl. No. 15/138,147, dated Nov. 8, 2017, 14 pages.
Notice of Acceptance received for Australian Patent Application No. 2009257368, dated Aug. 28, 2014, 2 pages.
Notice of Allowance received for Canadian Patent Application No. 2,727,429, dated May 26, 2015, 1 page.
Notice of Allowance received for U.S. Appl. No. 14/515,130, dated May 2, 2016, 8 pages.
Notice of Allowance received for U.S. Appl. No. 14/515,130, dated May 25, 2016, 3 pages.
Notice of Allowance received for U.S. Appl. No. 12/581,295, dated Jul. 10, 2015, 15 pages.
Notice of Allowance received for U.S. Appl. No. 12/581,295, dated Jul. 29, 2015, 7 pages.
Notice of Allowance received for U.S. Appl. No. 13/465,264, dated May 8, 2015, 7 pages.
Notice of Allowance received for U.S. Appl. No. 13/957,276, dated Aug. 28, 2015, 9 pages.
Notice of Allowance received for U.S. Appl. No. 14/271,276, dated Feb. 25, 2015, 8 pages.
Notice of Allowance received for U.S. Appl. No. 12/482,995, dated Dec. 24, 2014, 6 pages.
Notice of Allowance received for U.S. Appl. No. 13/049,199, dated Dec. 15, 2014, 7 pages.
Notice of Allowance received for U.S. Appl. No. 13/049,199, dated Jan. 13, 2015, 4 pages.
Notice of Allowance received for U.S. Appl. No. 13/646,570, dated Mar. 11, 2015, 7 pages.
Notice of Allowance received for U.S. Appl. No. 13/777,807, dated May 19, 2015, 13 pages.
Notice of Allowance received for U.S. Appl. No. 13/831,543, dated Oct. 8, 2014, 14 pages.
Notice of Allowance received for U.S. Appl. No. 14/061,554, dated Apr. 25, 2014, 8 pages.
Notice of Allowance received for U.S. Appl. No. 14/079,463, dated Apr. 1, 2014, 5 pages.
Notice of Allowance received for U.S. Appl. No. 14/218,858, dated Aug. 26, 2016, 8 pages.
Notice of Allowance received for U.S. Appl. No. 14/271,342, dated Mar. 13, 2015, 5 pages.
Notice of Allowance received for U.S. Appl. No. 13/615,107, dated Dec. 31, 2015, 10 pages.
Notice of Allowance received for U.S. Appl. No. 15/138,147, dated Dec. 5, 2018, 5 pages.
Notice of Allowance received for U.S. Appl. No. 15/138,147, dated Oct. 25, 2018, 7 pages.
Office Action received for Australian Patent Application No. 2009257368, dated Apr. 28, 2014, 4 pages.
Office Action received for Australian Patent Application No. 2009257368, dated Jul. 31, 2013, 4 pages.
Office Action received for Canadian Patent Application No. 2,727,429, dated Apr. 14, 2015, 4 pages.
Office Action received for Chinese Patent Application No. 201380033808.3, dated Jul. 5, 2016, 9 pages.
Office Action received for Chinese Patent Application No. 201380041656.1, dated Jul. 5, 2016, 9 pages.
Office Action received for Chinese Patent Application No. 201380042887.4, dated Aug. 8, 2016, 9 pages.
Office Action received for Japanese Patent Application No. 2011-513694, dated Aug. 27, 2013, 6 pages.
Office Action received for Japanese Patent Application No. 2011-513694, dated Jun. 10, 2014, 4 pages.

(56) References Cited

OTHER PUBLICATIONS

Office Action received for Japanese Patent Application No. 2014-158517, dated May 19, 2015, 5 pages.
Rosenschein et al., "Shock-Wave Thrombus Ablation, a New Method for Noninvasive Mechanical Thrombolysis", the American Journal of Cardiology, vol. 70, Nov. 15, 1992, pp. 1358-1361.
Zhong et al., "Transient Oscillation of Cavitation Bubbles Near Stone Surface During Electohydraulic Lithotripsy", Journal of Endourology, vol. 11, No. 1, Feb. 1997, pp. 55-61.
Intention to Grant received for European Patent Application No. 17705528.2, dated Oct. 21, 2019, 8 pages.
International Preliminary Report on Patentability received for PCT Patent Application No. PCT/US2017/016066, dated Nov. 8, 2018, 11 pages.
Office Action Received for Japanese Patent Application No. 2018-555589, dated Dec. 24, 2020, 7 pages (4 pages of English Translation and 3 pages of Official Copy).

* cited by examiner

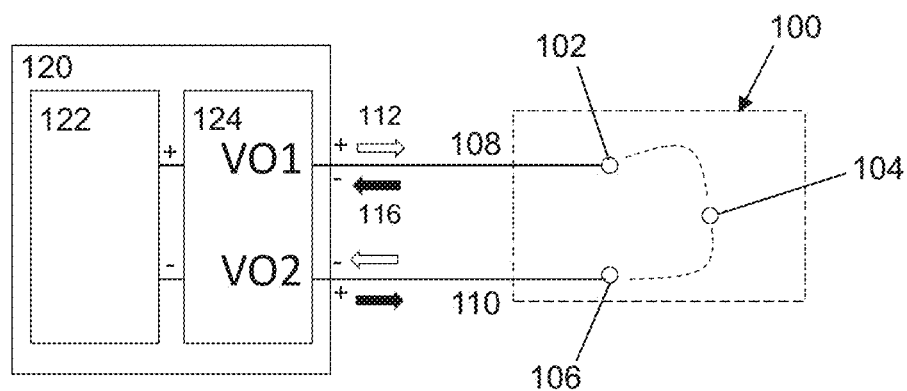
FIG. 1A
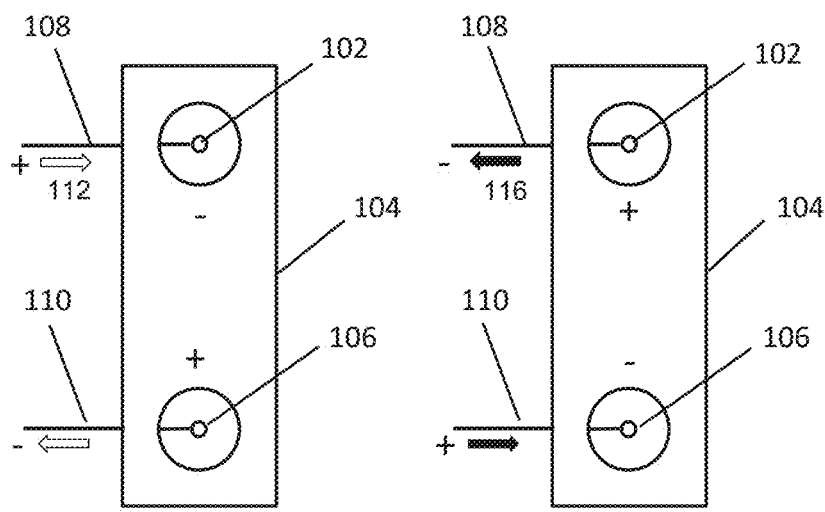
Positive Pulse      Negative Pulse
FIG. 1B      FIG. 1C

SHOCK WAVE DEVICE WITH POLARITY SWITCHING

CROSS-REFERENCE TO RELATED APPLICATIONS

This application is a continuation application of U.S. application Ser. No. 15/138,147, filed Apr. 25, 2016, also entitled SHOCK WAVE DEVICE WITH POLARITY SWITCHING, which is hereby incorporated by reference in its entirety for all purposes.

FIELD

The current invention relates to devices and methods for producing shock waves. The devices and methods may be used for angioplasty and/or valvuloplasty procedures.

BACKGROUND

Currently, angioplasty balloons are used to open calcified lesions in the wall of an artery. However, as an angioplasty balloon is inflated to expand the lesion in the vascular wall, the inflation pressure stores a tremendous amount of energy in the balloon until the calcified lesion breaks or cracks. That stored energy is then released and may stress and injure the wall of the blood vessel.

Electrohydraulic lithotripsy has been typically used for breaking calcified deposits or "stones" in the urinary or biliary track. Lithotripsy electrodes may similarly be useful for breaking calcified plaques in the wall of a vascular structure. Shock waves generated by lithotripsy electrodes may be used to selectively fracture a calcified lesion to help prevent sudden stress and injury to the vessel or valve wall when it is dilated using a balloon. It may therefore be useful to find improved ways to form shock waves in a balloon.

BRIEF SUMMARY

Described here are devices and methods for forming a shock wave in an angioplasty or valvuloplasty procedure. Generally, a shock wave device described here comprises an axially extending elongate member. The elongate member may comprise a first electrode pair comprising a first electrode and a second electrode. The electrode pair may be positioned within a conductive fluid. A controller may be coupled to the first electrode pair and may be configured to deliver a series of individual pulses to the first electrode pair such that each of the pulses creates a shock wave in the conductive fluid. The controller may cause current to flow through the electrode pair in a first direction for some of the pulses in the series and in a second direction opposite the first direction for the remaining pulses in the series. In some variations, the current may flow in the second direction for between twenty five percent and fifty percent of the pulses in the series. The shock wave devices and methods described herein may help facilitate the uniform and consistent delivery of energy to the electrodes, which may enhance the durability and performance of the electrodes.

In some variations, the controller may cause the current to flow in the second direction for between one third and half of the pulses in the series. In other variations, the controller may cause the current to flow in the second direction for at least about half of the pulses in the series.

In some variations, the controller may comprise a voltage polarity switch to switch a polarity of the electrodes between positive and negative. The electrodes may have opposite polarities. In other variations, a first surface area of a first conductive region of the first electrode may be smaller than a second surface area of a second conductive region of the second electrode.

In some variations, the controller may comprise a voltage source. A first wire may connect the first electrode to a first terminal of the voltage source, and a second wire may connect the second electrode to a second terminal of the voltage source. In some instances, the first terminal is positive and the second terminal is negative in the first direction of current flow, and the first terminal is negative and the second terminal is positive in the second direction.

In some variations, a second electrode pair may be provided and the controller may further comprise a multiplexer configured to selectively deliver the series of pulses to the first electrode pair and the second electrode pair. In other variations, the device may further comprise a fluid enclosure surrounding the electrode pair. The fluid enclosure may comprise a balloon surrounding a portion of the elongate member. The balloon may be configured to be filled with a conductive fluid, and the first electrode pair may be enclosed within and spaced from the balloon.

In yet other variations, the shock wave devices described here may comprise an axially extending elongate member. The elongate member may comprise a first electrode assembly comprising a first electrode pair and a second electrode pair. The first electrode assembly may be positioned within a conductive fluid. A controller may be coupled to the first electrode assembly and configured to deliver a series of individual pulses to the first electrode assembly such that each of the pulses creates a shock wave in the conductive fluid. The controller may cause current to flow through the electrode assembly in a first direction for some of the pulses in the series and in a second direction opposite the first direction for the remaining pulses in the series. In some instances, the current flows in the second direction for between twenty five percent and fifty percent of the pulses in the series.

In some variations, the first electrode assembly may comprise a first electrode, a second electrode, and a common electrode. The first electrode pair may comprise the first electrode and the common electrode and the second electrode pair may comprise the second electrode and the common electrode. In some instances, the controller may comprise a voltage polarity switch to switch a polarity of the first electrode and the second electrode between positive and negative. The first electrode and the second electrode may have opposite polarities. In other instances, a first surface area of a first conductive region of the first electrode and a second surface area of a second conductive region of the second electrode may be different than a third surface area of a third conductive region of the common electrode. In some instances, the controller may comprise a voltage source where a first wire may connect the first electrode to a first terminal of the voltage source, and a second wire may connect the second electrode to a second terminal of the voltage source. In other instances, the controller may comprise a voltage source where a first wire may connect the first electrode to a first terminal of the voltage source, a second wire may connect the second electrode to a second terminal of the voltage source, and a third wire may connect the common electrode to a third terminal of the voltage source.

In some variations, a second electrode assembly may be coupled in series to the first electrode assembly. In some instances, the controller may comprise a voltage source where a first wire may connect the first electrode assembly to a first terminal of the voltage source, a second wire may connect the first electrode assembly to the second electrode assembly, and a third wire may connect the second electrode assembly to a second terminal of the voltage source.

In other variations, the device may comprise a second electrode assembly. The controller may further comprise a multiplexer that selectively delivers the series of pulses to the first electrode assembly and the second electrode assembly. In yet other variations, the device may further comprise a fluid enclosure surrounding the first electrode assembly. The fluid enclosure may comprise a balloon surrounding a portion of the elongate member. The balloon may be configured to be filled with a conductive fluid, and the first electrode assembly may be enclosed within and spaced from the balloon.

In some variations, methods of forming shock waves described here may comprise advancing a shock wave device into a blood vessel. The shock wave device may comprise an axially extending elongate member. The elongate member may comprise a first electrode pair comprising a first electrode and a second electrode. The first electrode pair may be positioned within a conductive fluid. A series of individual pulses may be delivered to the first electrode pair to create shock waves in the conductive fluid to cause current to flow through the electrode pair in a first direction for some of the pulses in the series and in a second direction opposite the first direction for the remaining pulses in the series. In some variations, the current may flow in the second direction for between twenty five percent and fifty percent of the pulses in the series.

In some variations, the current may flow in the second direction for between one third and half of the pulses in the series. In other variations, the current may flow in the second direction for at least about half of the pulses in the series. In some variations, a voltage pulse width may be measured to monitor a condition of the shock wave device. In some of these variations, the percentage of pulses that cause current to flow in the second direction may be adjusted according to the measured voltage pulse width.

BRIEF DESCRIPTION OF THE DRAWINGS

FIGS. 1A-1D are illustrative depictions of a variation of an electrode assembly. FIGS. 1A and 1D are block diagrams of variations of a controller coupled to an electrode assembly. FIGS. 1B and 1C are illustrative depictions of variations of a flattened electrode assembly.

FIG. 2A is a block diagram of a variation of a controller coupled to the series of electrode assemblies. FIG. 2B is an illustrative depiction of a variation of flattened electrode assemblies.

FIG. 6A is a top view and FIG. 6B is a bottom view of a variation of the electrode assembly. FIG. 6C is a perspective view of a variation of a common electrode.

FIG. 7A is a top view and FIG. 7B is a bottom view of a variation of the series of electrode assemblies.

DETAILED DESCRIPTION

Figure 1D:
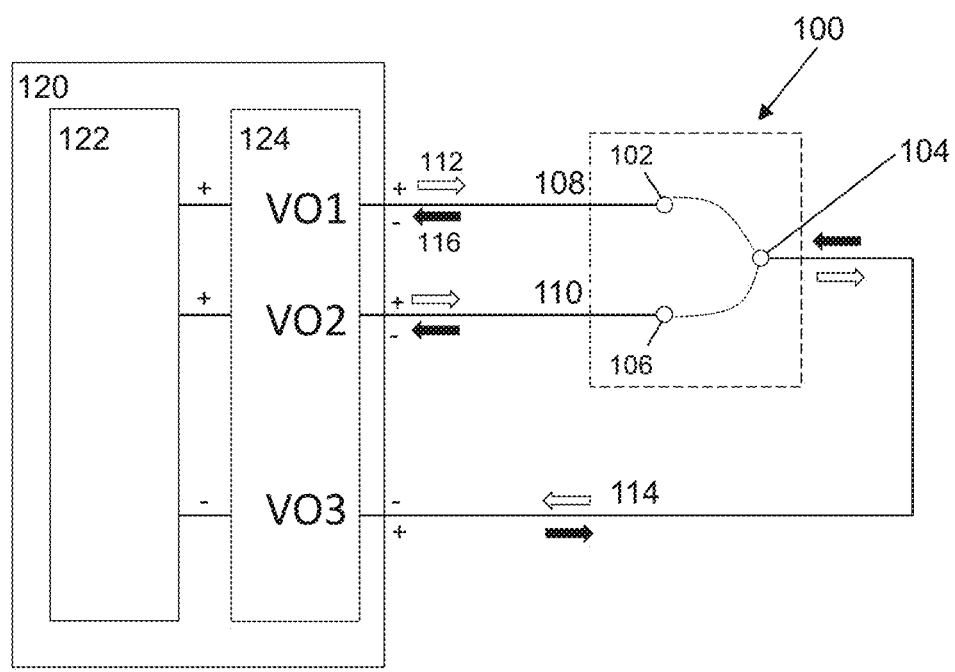

Described herein are devices and systems that comprise one or more shock wave electrodes that may be suitable for use in angioplasty and/or valvuloplasty procedures. Generally, shock wave electrodes are provided along an axially extending elongate member (e.g., catheter) and may be attached to a source of high voltage pulses, ranging from 0.1 kV to 10 kV for various pulse durations. In some variations, the electrodes may be surrounded by an enclosure carrying a conductive fluid (e.g., saline). In some variations, the enclosure may comprise a balloon surrounding a portion of the elongate member and configured to be filled with a conductive fluid, where the electrodes may be enclosed within and spaced from the balloon walls.

A controller may be coupled to the first electrode pair to deliver a series of energy pulses to produce shock waves. The shock waves generated may disrupt calcified obstructions in an artery or a valve. One mechanism for shock wave formation is described below. When a high voltage is applied across a pair of electrodes located within the conductive fluid, a plasma arc may form between them, giving rise to a steam bubble in the fluid. A first shock wave may occur when the steam bubble first forms and a second shock wave may occur as the steam bubble collapses. Shock waves may be mechanically conducted through the fluid to apply mechanical force or pressure to break apart any calcified plaques on, or in, the vasculature walls.

The size, rate of expansion, and collapse of the bubble (and therefore, the magnitude, duration, and distribution of the mechanical force) may vary based on the magnitude and duration of the voltage pulse. Furthermore, the timing and size of the bubble, along with the sonic output and propagation direction of the resultant shock waves, depend at least in part on the location, geometry, size, condition, and distances between the electrodes (electrode gap distance). For example, an increase in electrode gap distance decreases the corresponding sonic output. The size and arrangement of the electrodes may also impact the types of vascular structures that may be accessed and treated by a shock wave device. Shock wave electrodes may be made of materials that can withstand high voltage levels and intense mechanical forces (e.g., about 300-3000 psi or 20-200 ATM in a few microseconds) that may be generated during use. For example, the electrodes may be made of stainless steel, tungsten, nickel, iron, steel, and the like.

Generally, current flowing between a pair of electrodes in a conductive fluid causes movement of metal from the positive terminal to the negative terminal, eventually depleting the positive terminal electrode of material, and may be referred to as one-sided erosion when a direction of current flow is fixed. Shock wave electrodes may experience a high rate of wear and erosion with every pulse applied due to the necessarily high current (e.g., hundreds of amps) flowing through the fluid, heat generated by the plasma arc, and mechanical shock wave forces.

The devices, systems, and methods described herein may help to reduce the rate of electrode wear to enhance electrode durability and shock wave consistency. The longevity of an electrode pair may depend on at least one of the following: polarity of a voltage pulse, length of a voltage pulse, magnitude of a voltage pulse, material properties, fluid conductivity, electrode gap distance between conductive regions of each of the electrodes in an electrode pair, and/or the surface area of the conductive region(s) of the electrodes in the pair. A longer pulse may increase the wear/erosion of an electrode pair as compared to a shorter pulse. In some variations where the electrode pair has different sized electrodes where one electrode has a smaller conductive region surface area than the other electrode, the electrode with the smaller conductive region may be more susceptible to erosion than the electrode with a larger conductive region. That is, the electrode with the smaller conductive region may erode at a greater rate than the electrode with the larger conductive region. The devices and methods described herein may help to even out the rate of erosion between the electrodes in an electrode pair, so that the electrodes erode at approximately the same rate. This may enhance the durability of the overall electrode pair, and may also facilitate uniform energy delivery to the electrode pair over a greater number of pulses.

It should be appreciated that a shock wave device generates the strongest shock waves when the electrodes are dissimilar in size where the smaller electrode has a positive polarity and the larger electrode has a negative polarity. Thus, while an electrode pair having a small, positive terminal electrode and a large, negative terminal electrode may form the strongest shock wave, this combination of size and polarity may shorten the lifetime of the electrode pair. The problem of a short lifespan may not be a simple matter of increasing electrode size since the size of a shock wave device and electrodes may be limited by the size of the vasculature through which it is advanced. However, voltage polarity switching, as described in further detail below, may facilitate electrode longevity while maintaining electrode size such that the electrode can be navigated through vasculature. Additionally or alternatively, voltage polarity switching may facilitate a reduction in electrode size with a similar electrode longevity relative to a non-polarity switching device.

Furthermore, the devices, systems, and methods described herein may facilitate the uniformity of shock wave intensity formed at different sites along a shock wave device. In some variations, a shock wave device may comprise a plurality of spaced apart electrode pairs connected in series. The shock waves generated by the electrode pairs may vary in strength even if the size and shape of the electrode pairs are the same. For instance, identical electrode pairs in series positioned 180 degrees apart from each other may form shock waves of varying strength from opposing sides of the device. This difference may be negligible for any single pulse. However, over a series of pulses, one side of the shock wave device may be more effective at cracking calcium deposits than the other side of the device. Voltage polarity switching, as described in further detail below, may facilitate the uniformity of shock wave intensity formed in different electrode pairs.

For example, a controller may cause current to flow through an electrode pair in a first direction for some pulses and in a second direction that is opposite to the first direction for other pulses. As an example, the direction of current flow may vary pulse to pulse or every second pulse, and is not particularly limited. It should be noted that the pulses are outputted discretely such that there is an interval of time between pulses when current does not flow through a shock wave device. The duration of the interval of time may be pre-selected according to, for example, a desired rate or frequency of shock wave generation. Furthermore, each pulse has a single direction of current flow and does not switch within the pulse. For instance, a voltage polarity switch may switch only when current is not flowing to the shock wave device (i.e., the voltage polarity switch may only occur in the interval between voltage pulses, and not during a voltage pulse).

Furthermore, the direction of current flow may vary randomly for each pulse so long as the total number of pulses maintain a predetermined current flow direction ratio. For example, for a set of 50 pulses being split evenly in the first direction and the second direction, the direction of current flow need not switch every pulse. As an illustrative example, 20 pulses in the first direction may be followed by 10 pulses in the second direction, then 3 pulses in the first direction, 15 pulses in the second direction, and 2 pulses in the first direction. Accordingly, while the total number of pulses is split evenly between the first and second direction, the number of switches in current flow does not necessarily correspond to the current flow ratio direction.

In some variations, a single pulse may be provided in the second direction with the remaining pulses in the first direction, and vice-versa. This allows the electrode pair to produce shock waves with a greater number of pulses before failure relative to an electrode pair receiving pulses with a constant polarity. Durability may thus be improved by distributing the electrode wear of the positive pulse over both electrodes.

In one variation, the current may flow in a first direction for about half of the pulses in the series and in the second, opposite direction for about the other half of the pulses in the series. In doing so, each electrode is set to be the positive terminal for about half of the pulses, thereby distributing the number of high erosion positive pulses experienced by any one of the electrodes about equally between the electrodes in the pair. The direction of current flow may be switched one or more times. In some cases, the electrode pair longevity may be about doubled relative to electrodes having a single direction of current flow, allowing more shock waves to be formed and/or the electrode pair to be formed smaller relative to electrodes having a single direction of current flow. Therefore, the shock wave devices described herein may be particularly useful in small arteries such as coronary arteries. Moreover, a shock wave device comprising a plurality of electrode pairs having pulses with current flow in both directions may facilitate the uniformity of shock wave intensity generated by the electrode pairs.

I. Devices

Generally described here are shock wave devices for angioplasty and/or valvuloplasty procedures. The devices and methods described here may use one or more devices or elements described in U.S. Pat. No. 8,888,788 and titled "LOW PROFILE ELECTRODES FOR AN ANGIOPLASTY SHOCK WAVE CATHETER," and/or one or more devices or elements described in U.S. Pat. No. 9,011,463 and titled "SHOCK WAVE BALLOON CATHETER WITH MULTIPLE SHOCK WAVE SOURCES," each of which is hereby incorporated by reference in its entirety.

FIG. 1A is a block diagram of a controller 120 coupled to an electrode assembly 100. Electrode assembly 100 may comprise a first electrode 102, a second electrode 104, and a third electrode 106. The first electrode 102 may be connected to a first voltage output terminal V01 of a voltage source of the controller 120 by first wire 108, the third electrode 106 may be connected to a second voltage output terminal V02 of a voltage source of the controller 120 by a second wire 110, and the second or common electrode 104 may be provided in series between the first electrode 102 and third electrode 106. Upon application of a sufficient voltage pulse, a first plasma arc may form between the first electrode 102 and the second electrode 104 (i.e., a first electrode pair), and a second plasma arc may form between the second electrode 104 and the third electrode 106 (i.e., a second electrode pair). The first and second electrode pairs are connected in series, where the second electrode 104 is shared between the first and second electrode pairs. Although electrode assembly 100 is described above as comprising three electrodes that form two electrode pairs, some variations of an electrode assembly may comprise two electrodes that form one electrode pair.

A first direction of current flow 112 of an energy pulse may be delivered to the electrode assembly 100 by a voltage source 122 of the controller 120. The controller 120 may cause other pulses delivered to the electrode assembly 100 to have a second direction 116 of current flow that is the opposite direction of the first direction 112. The controller 120 may select a direction of current flow, and thus the voltage polarity of the electrodes, for each pulse delivered to the electrode assembly 100. In order to select a direction of current flow, the controller 120 may comprise a voltage polarity switch 124 to switch a polarity of the electrodes 102, 106 between positive and negative where the electrodes 102, 106 have opposite polarities.

In some variations, for a series of pulses, the controller may cause current to flow through the electrode pair in a first direction for some of the pulses in the series and in a second direction opposite the first direction for the remaining pulses in the series. In one variation, a first direction of current flow may be provided for at least one of the pulses. In another variation, a first direction of current flow may be provided for at least about 5% of the pulses. In another variation, a first direction of current flow may be provided for at least about 10% of the pulses. In another variation, a first direction of current flow may be provided for at least about 15% of the pulses. In another variation, a first direction of current flow may be provided for at least about 20% of the pulses. In another variation, a first direction of current flow may be provided for at least about 25% of the pulses. In another variation, a first direction of current flow may be provided for at least about 30% of the pulses. In yet another variation, a first direction of current flow may be provided for at least about a third of the pulses. In another variation, a first direction of current flow may be provided for at least about 40% of the pulses. In another variation, a first direction of current flow may be provided for at least about 45% of the pulses. In still another variation, a first direction of current flow may be provided for at least about half of the pulses.

In still other variations, the ratio of current flow of the pulses in the first direction to the second direction may be about 1:6. In another variation, the ratio of current flow of the pulses in the first direction to the second direction may be about 5:6. In another variation, the ratio of current flow of the pulses in the first direction to the second direction may be about 1:8. In another variation, the ratio of current flow of the pulses in the first direction to the second direction may be about 3:8. In another variation, the ratio of current flow of the pulses in the first direction to the second direction may be about 5:8. In another variation, the ratio of current flow of the pulses in the first direction to the second direction may be about 7:8. In another variation, the ratio of current flow of the pulses in the first direction to the second direction may be about 1:9. In another variation, the ratio of current flow of the pulses in the first direction to the second direction may be about 2:9. In another variation, the ratio of current flow of the pulses in the first direction to the second direction may be about 4:9. In another variation, the ratio of current flow of the pulses in the first direction to the second direction may be about 5:9. In another variation, the ratio of current flow of the pulses in the first direction to the second direction may be about 7:9. In another variation, the ratio of current flow of the pulses in the first direction to the second direction may be about 8:9. In another variation, the ratio of current flow of the pulses in the first direction to the second direction may be about 1:12. In another variation, the ratio of current flow of the pulses in the first direction to the second direction may be about 1:16. In another variation, the ratio of current flow of the pulses in the first direction to the second direction may be about 1:32.

It should be appreciated that these examples are non-limiting. For example, the controller may provide current delivery in a first direction for every pulse except for one pulse provided in the second direction, and vice versa. The number of pulses in each direction of current flow (e.g., ratio of current flow of first direction to second direction) may be determined based on a desired longevity of the shock wave device, shock wave uniformity, shock wave energy, and so forth. In some variations, a first direction of current flow provided for about half of the pulses may maximize the longevity of the shock wave device.

The number of transitions between current flow directions is not particularly limited. In some instances, the direction of current flow may be switched according to the ratio of pulses in the first direction to the second direction. For example, the direction of current flow may transition every pulse when there are an equal number of positive and negative pulses. However, the direction of current flow may also vary randomly for each pulse so long as the total number of pulses maintains a predetermined ratio of current flow direction. Accordingly, the direction of current flow need not switch for every pulse even if the number of pulses in each direction is equal. As another example, alternating on average the direction of current flow of the pulses may about double the durability of the smaller electrodes, and thus the lifetime of the electrode assembly. Even when the electrodes in an electrode pair are of equal size, alternating the direction of current flow so that each electrode receives about the same number of positive pulses will distribute the wear over two electrodes so as to about double the durability of the electrode pair relative to electrodes receiving a single direction of current. It should be noted that polarity switching of any number of pulses aids durability (e.g., the number of shock waves the electrode generates before electrode failure).

Figures 9A, 9B:
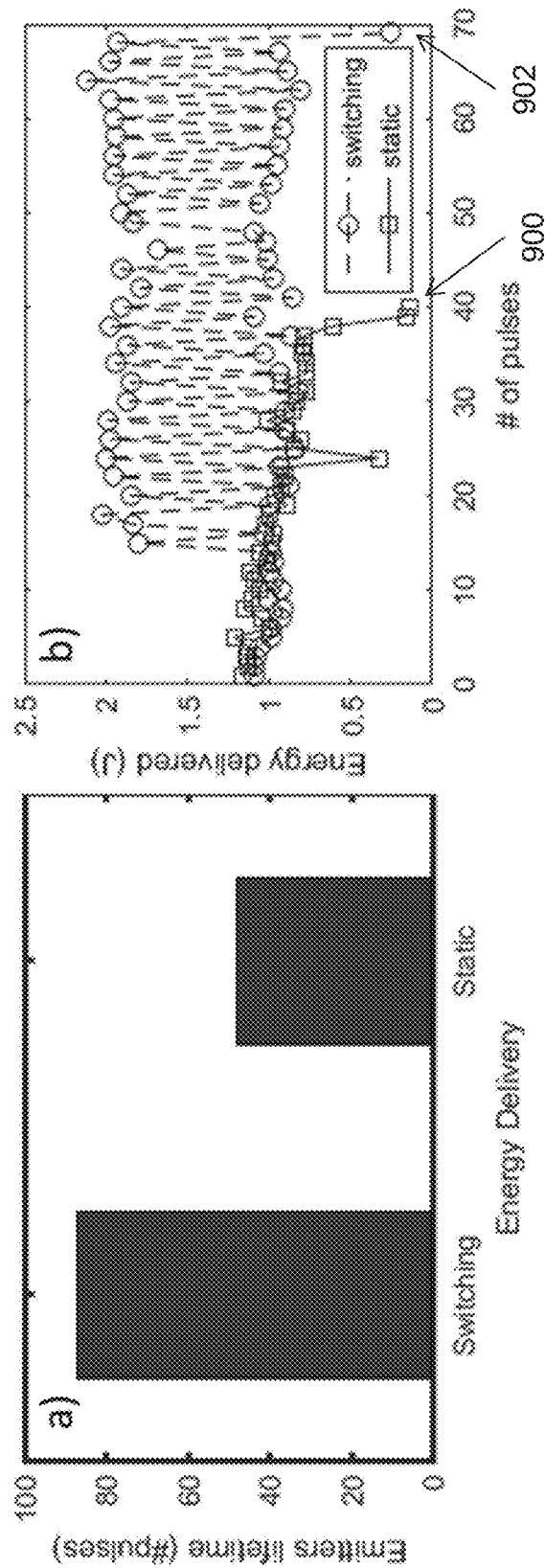
FIG. 9A is an illustrative graph of pulse number as a function of voltage polarity.
FIG. 9B is an illustrative graph of energy delivered at the electrode assembly as a function of pulse number between switching and non-switching energy pulses.

Moreover, shock waves output from different electrode pairs may facilitate uniformity of shock wave forces between the shock wave sites on average as polarity switching allows each electrode pair to receive the positive pulse. This allows more predictable results with a higher average shock wave strength delivered at each shock wave site. For example, FIG. 9B is an illustrative graph of energy delivered as a function of pulse number for a static (constant polarity) shock wave device and a switching (alternating polarity)

shock wave device. In FIG. 9B, the electrical energy delivered by the polarity-switching shock wave device is higher on average per pulse and decays less than the energy delivered to the constant polarity device. The electrical energy delivered may be positively correlated with shock wave strength.

Next, the second electrode 104 illustrated in FIGS. 1B and 1C may have a cylindrical or ring shape, similar to that depicted in FIG. 6C as discussed in further detail below. However, for the ease of explanation, FIGS. 1B and 1C depict a flattened second electrode 104 to illustrate the different voltage polarities that may be applied to the electrode assembly 100. In FIG. 1B, the controller 120 may output one or more positive pulses in a first direction 112 of current flow where the first wire 108 is coupled to a positive terminal of a voltage source 122 of the controller 120 and the first electrode 102, and the second wire 110 is coupled to a negative terminal of a voltage source of the controller 120 and the third electrode 106. In use, the application of the voltage pulse creates a plasma in the fluid that extends across the electrode pairs and permits conduction of the current. The current then flows from the first electrode 102 to second electrode 104, and then to third electrode 106. Plasma formation thus creates two electrode pairs connected in series. As discussed above, the positive terminal first electrode 102 may experience a higher rate of wear than the negative terminal third electrode 106 when receiving a positive pulse from the controller 120.

Conversely, in FIG. 1C, a negative terminal first electrode 102 may deplete less material than the positive terminal third electrode 106 when receiving a negative pulse in a second direction 116 of current flow from a voltage source 122 of the controller 120. In order to distribute the wear between the first electrode 102 and third electrode 106 more evenly, the controller 120 may cause a current to flow in a first direction 112 for some of the pulses (FIG. 1B) and in a second direction 116 opposite the first direction 112 for the other pulses (FIG. 1C). As a consequence, the electrode assembly 100 may form a greater number of shock waves with improved consistency before one or both of the smaller electrodes (102, 106) are depleted and the electrode assembly 100 fails.

Furthermore, as shown in FIGS. 1B and 1C, the first electrode 102 and the third electrode 106 will have opposite voltage polarities no matter the direction of current flow. Therefore, the strength of the shock waves formed by the first electrode pair and the second electrode pair will differ for every pulse. In the illustrated embodiment, the conductive region of the first electrode 102 and the third electrode 106 may be smaller than the conductive region of the second electrode 104. Accordingly, the first electrode pair receiving the positive pulse 112 (FIG. 1B) may generate a stronger shock wave than the second electrode pair. Similarly, the first electrode pair receiving the negative pulse 116 may generate a weaker shock wave than the second electrode pair.

However, by alternating positive and negative pulses to the electrode assembly 100, the average shock wave strength output by the first electrode pair and the second electrode pair may be more uniform to reduce variability. This may provide more consistent and predictable treatment by the shock wave device such that a practitioner may not need to align the shock wave device in vasculature based on differences shock wave strength between electrode pairs.

FIG. 1D is a block diagram of another variation of a controller 120 coupled to the electrode assembly 100. The electrode assembly 100 may comprise a first electrode 102, second electrode 104, and a third electrode 106. The first electrode 102 and second or common electrode 104 form a first electrode pair, and the third electrode 106 and the second electrode 104 form a second electrode pair. A first direction of current flow 112 of an energy pulse may be delivered to the electrode assembly 100 by a voltage source 122 of the controller 120. The controller 120 may cause other pulses delivered to the electrode assembly 100 to have a second direction of current flow 116 opposite the first direction 112 through the electrode assembly 100. The voltage polarity switch 124 of the controller 120 may select a direction of current flow, and thus the voltage polarity of the electrodes, for each pulse delivered to the electrode assembly 100.

In FIG. 1D, the first electrode 102 may be connected to a first voltage output terminal V01 of a voltage source 122 of the controller 120 by first wire 108, the third electrode 106 may be connected to a second voltage output terminal V02 of a voltage source 122 of the controller 120 by a second wire 110, and the second electrode 104 may be connected to a third voltage output terminal V03 (ground channel) of a voltage source 122 of the controller 120 by a third wire 114. In some variations, the first voltage output terminal V01 and the second voltage output terminal V02 may be positive channels while the third voltage output terminal V03 may be a negative channel for some of the pulses. The controller 120 may also set the first voltage output terminal V01 and the second voltage output terminal V02 to be negative channels while the third voltage output terminal V03 may be a positive channel for the remaining pulses.

During a high voltage pulse on the first and/or second voltage output terminals V01, V02, current may flow in the first direction 112 or the second direction 116 over the first wire 108 and/or second wire 110 to respective first electrode 102 and third electrode 106. The voltage source 122 of controller 120 may apply a positive or negative pulse on output terminal V01 such that the potential difference between the first electrode 102 and the second electrode 104 is large enough to form a plasma arc between them, generating a bubble that gives rise to a shock wave. Similarly, the voltage source of the controller 120 may simultaneously or sequentially apply a positive or negative energy pulse on output terminal V02 such that the potential difference between the third electrode 106 and the second electrode 104 is large enough to form a plasma arc between them, generating a bubble that gives rise to a different shock wave. In some variations, when energy pulses are applied to output terminals V01 and V02 simultaneously, a first shock wave formed between the first electrode 102 and the second electrode 104 and a second shock wave formed between the third electrode 106 and the second electrode 104 may be formed simultaneously.

Where the first electrode 102 and third electrode 106 are located circumferentially opposite to each other (e.g., 180 degrees apart from each other around the circumference of the elongate member), the shock waves generated by the first and second electrodes pairs may propagate in opposite directions, extending outward from the sides of a shock wave device. The current that traverses the bubble from the first electrode 102 and/or the third electrode 106 to the second electrode 104 may return via third wire 114 to voltage output terminal V03 (which may be a ground channel). Voltage output terminals V01 and V02 may be independently addressed (e.g., voltage and current may be applied to one output but not necessarily the other), or may not be independently addressed (e.g., activating one output necessarily activates the other).

Figure 2A:
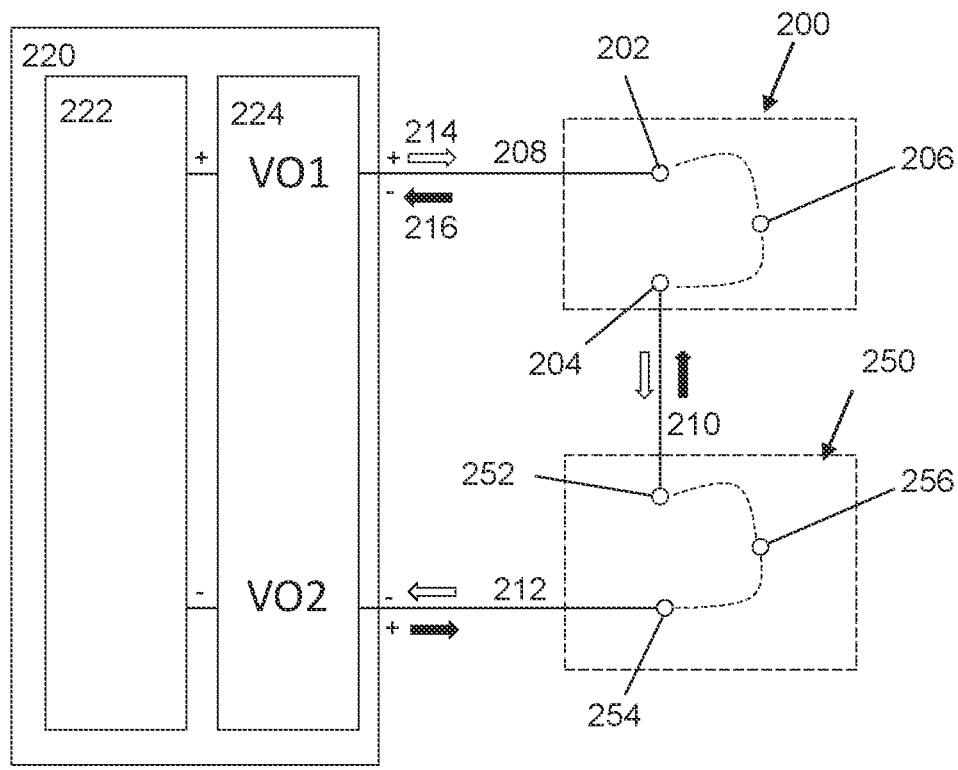
FIGS. 2A-2B are illustrative depictions of a variation of a series of electrode assemblies.

In another variation, FIG. 2A is a block diagram of a controller 220 coupled to the first and second electrode assemblies 200, 250. The first electrode 202 and the first common electrode 206 form a first electrode pair that may generate a first shock wave, and the second electrode 204 and the first common electrode 206 form a second electrode pair that may generate a second shock wave. Likewise, the third electrode 252 and the second common electrode 256 form a third electrode pair that may generate a third shock wave, and the fourth electrode 254 and the second common electrode 256 form a fourth electrode pair that may generate a fourth shock wave.

The first, second, third, and fourth electrode pairs may be connected in a series configuration and receive a series of pulses. A first direction of current flow 214 of some of the pulses in the series may be delivered to the first and second electrode assemblies 200, 250 by a voltage source 222 of the controller 220. The controller 220 may cause the remaining pulses in the series that are delivered to the first and second electrode assemblies 200, 250 to have a second direction 216 of current flow through the electrode assemblies 200, 250. A voltage polarity switch 224 of the controller 220 may select a direction of current flow, and thus the voltage polarity of the electrodes, for each pulse delivered to the electrode assemblies 200, 250. For instance, the voltage polarity switch 224 may switch a polarity of the first electrode 202 and fourth electrode 254 between positive and negative, where the first electrode 202 and fourth electrode 254 have opposite polarities.

In some variations, for a series of pulses, the controller may cause current to flow through the electrode pair in a first direction for some of the pulses in the series and in a second direction opposite the first direction for the remaining pulses in the series. In one variation, a first direction of current flow may be provided for at least one of the pulses. In another variation, a first direction of current flow may be provided for at least about 5% of the pulses. In another variation, a first direction of current flow may be provided for at least about 10% of the pulses. In another variation, a first direction of current flow may be provided for at least about 15% of the pulses. In another variation, a first direction of current flow may be provided for at least about 20% of the pulses. In another variation, a first direction of current flow may be provided for at least about 25% of the pulses. In another variation, a first direction of current flow may be provided for at least about 30% of the pulses. In yet another variation, a first direction of current flow may be provided for at least about a third of the pulses. In another variation, a first direction of current flow may be provided for at least about 40% of the pulses. In another variation, a first direction of current flow may be provided for at least about 45% of the pulses. In still another variation, a first direction of current flow may be provided for at least about half of the pulses.

In still other variations, the ratio of current flow of the pulses in the first direction to the second direction may be about 1:6. In another variation, the ratio of current flow of the pulses in the first direction to the second direction may be about 5:6. In another variation, the ratio of current flow of the pulses in the first direction to the second direction may be about 1:8. In another variation, the ratio of current flow of the pulses in the first direction to the second direction may be about 3:8. In another variation, the ratio of current flow of the pulses in the first direction to the second direction may be about 5:8. In another variation, the ratio of current flow of the pulses in the first direction to the second direction may be about 7:8. In another variation, the ratio of current flow of the pulses in the first direction to the second direction may be about 1:9. In another variation, the ratio of current flow of the pulses in the first direction to the second direction may be about 2:9. In another variation, the ratio of current flow of the pulses in the first direction to the second direction may be about 4:9. In another variation, the ratio of current flow of the pulses in the first direction to the second direction may be about 5:9. In another variation, the ratio of current flow of the pulses in the first direction to the second direction may be about 7:9. In another variation, the ratio of current flow of the pulses in the first direction to the second direction may be about 8:9. In another variation, the ratio of current flow of the pulses in the first direction to the second direction may be about 1:12. In another variation, the ratio of current flow of the pulses in the first direction to the second direction may be about 1:16. In another variation, the ratio of current flow of the pulses in the first direction to the second direction may be about 1:32.

In some variations, the number of pulses in each direction of current flow (e.g., ratio of current flow of first direction to second direction) may be determined based on a desired longevity of the shock wave device, shock wave uniformity, shock wave energy, material properties, electrode gap distance, fluid conductivity, and so forth. In some instances, the direction of current flow may be switched according to the ratio of pulses in the first direction to the second direction. In other instances, the direction of current flow may vary randomly for each pulse so long as the total number of pulses maintains a predetermined ratio of current flow direction.

Furthermore, shock waves output from the first through fourth electrode pairs may have more uniform strength on average as polarity switching allows each electrode pair to receive positive pulses. This allows more predictable results, with a greater amount of electrical energy delivered to each electrode pair, which may facilitate the generation of stronger shock waves. Thus, a shock wave device may be able to more uniformly apply mechanical forces/pressures regardless of its orientation within the vasculature.

Figure 2B:
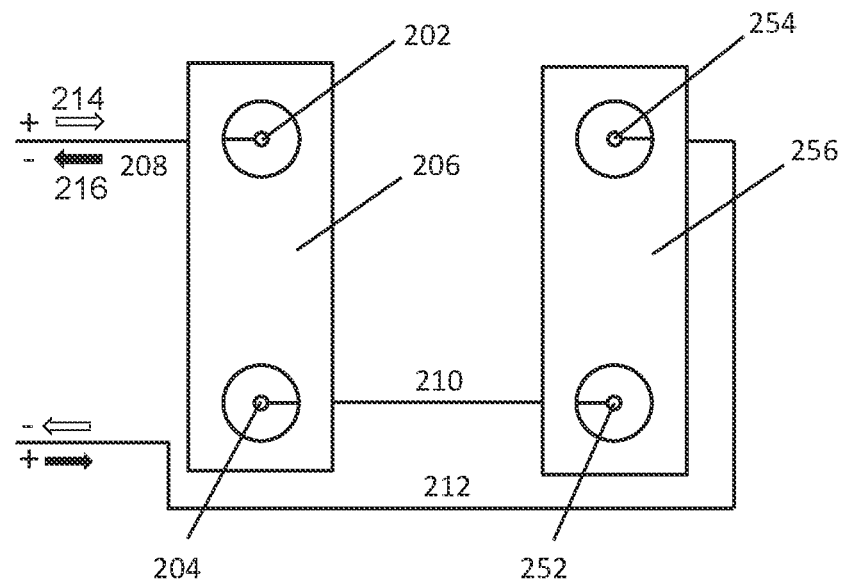

The first and second common electrodes 206, 256 illustrated in FIG. 2A may in some variations have a cylindrical or ring shape, similar to that depicted in FIG. 6C as discussed in further detail below. However, for the ease of explanation, FIG. 2B depicts flattened first and second common electrodes 206, 256 to illustrate the different voltage polarities that may be applied to the first and second electrode assemblies 200, 250. A voltage source 222 of the controller 220 may output one or more pulses where the first wire 208 is coupled to a positive terminal V01 of controller 220 and the third wire 212 is coupled to a negative terminal V02 of controller 220. The second electrode 204 may be connected to the third electrode 252 via a second wire 210 (e.g., an interconnect wire). In this configuration, the first and second electrode assemblies 200, 250 receive a positive pulse where the first and third electrode pairs generate stronger shock waves than the second and fourth electrode pairs.

Conversely, a voltage source 222 of the controller 220 may output one or more pulses where the first wire 208 is coupled to a negative terminal V01 of controller 220 and the third wire 212 is coupled to a positive terminal V02 of controller 220. In this configuration, the first and second electrode assemblies 200, 250 receive a negative pulse where the second and fourth electrode pairs generate the stronger shock waves. Therefore, in order to distribute the wear between the electrodes of the first and second electrode assemblies 200, 250 more evenly, the voltage polarity switch 224 of the controller 220 may cause a current to flow in a first direction for some of the pulses in a series of pulses and in a second direction opposite the first direction for the remaining pulses in the series. As a consequence, the electrode assemblies 200, 250 may form a greater number of shock waves before one or more of the smaller inner electrodes (202, 204, 252, 254) are depleted, as well as more uniform shock waves propagated on average from the electrode assemblies (200, 250).

Figure 3:
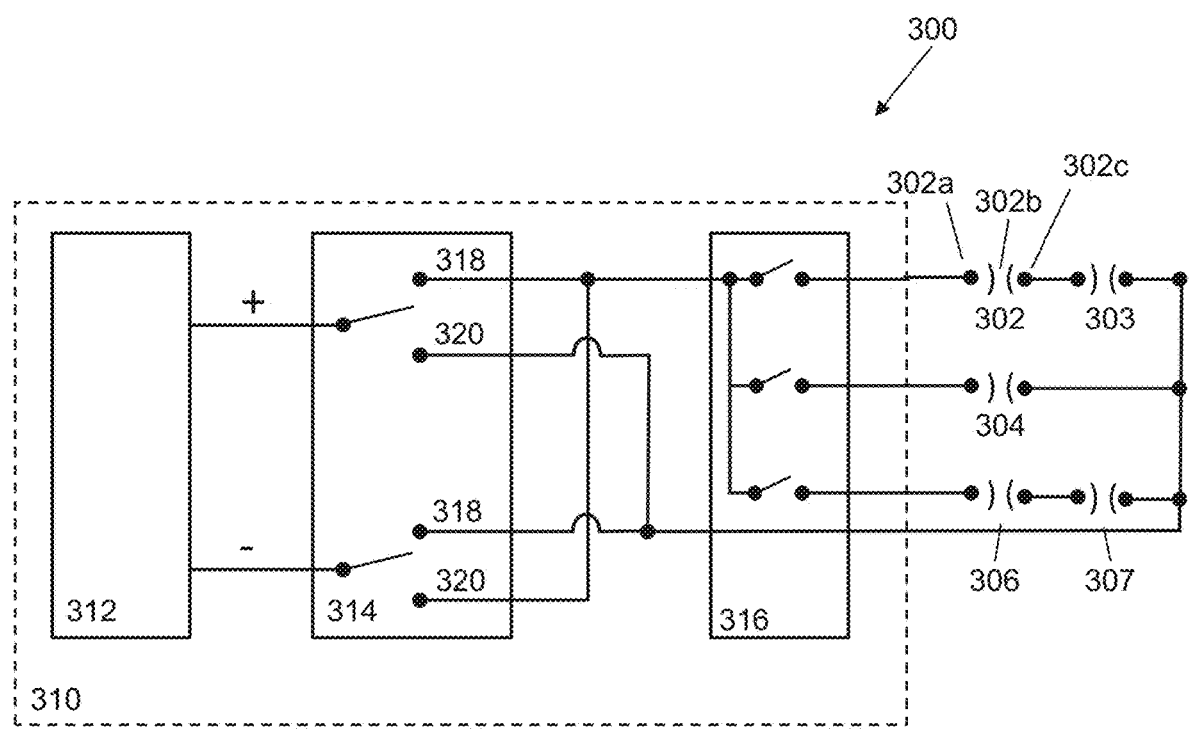
FIG. 3 is an illustrative block diagram of a variation of a shock wave system comprising electrode assemblies, a controller, and a voltage source.

FIG. 3 is an illustrative block diagram of a variation of a shock wave system 300 comprising a first electrode assembly 302, a second electrode assembly 303, a third electrode assembly 304, fourth electrode assembly 306, and fifth electrode assembly 307. The first electrode assembly 302 may comprise a first electrode 302a, second electrode 302b, and a third electrode 302c having a structure analogous to first electrode 102, second electrode 104, and third electrode 106, respectively, as depicted in FIGS. 1A and 1B. As denoted symbolically in FIG. 3, the conductive surface areas of the first electrode 302a and third electrode 302c may be smaller relative to the conductive surface areas of the second electrode 302b. In other variations, the larger electrode 302b may comprise individual electrodes connected by, for example, an interconnect wire. The second through fifth electrode assemblies 303, 304, 306, and 307 may comprise a similar configuration of electrodes as first electrode assembly 302.

The first and second electrode assemblies 302 and 303 are connected in series. The fourth and fifth electrode assemblies 306, 307 are connected in series. As shown in FIG. 3, the electrode assemblies 302, 303, 304, 306, and 307 are switchably connected in parallel to a controller 310. The controller 310 may comprise a voltage source 312 to deliver pulses to the electrode assemblies 302, 303, 304, 306, and 307. A multiplexer 316 of the controller 310 may selectively activate first and second electrode assemblies 302 and 303, third electrode assembly 304, and fourth and fifth electrode assemblies 306 and 307. The multiplexer 316 may be configured to selectively connect the voltage source 312 across the parallel electrode assembly lines individually, one at a time, or in any combination. The controller 310 may further comprise a voltage polarity switch 314 configured to provide a first direction of current flow corresponding to a first switch position 318 and a second direction of current flow opposite the first direction, the second direction corresponding to a second switch position 320.

For example, the voltage source 312 outputs a predetermined voltage pulse to the voltage polarity switch 314. In the switch 314, a direction of current flow is selected between a first direction of current flow and a second direction opposite the first direction. The multiplexer 316 may receive the energy pulse in either the first direction or the second direction, and then selectively deliver a series of pulses, having the current flow direction selected by the voltage polarity switch 314, to the electrode assemblies 302, 303, 304, 306, and 307 as illustrated in the timing diagram of FIG. 4.

Figure 4:
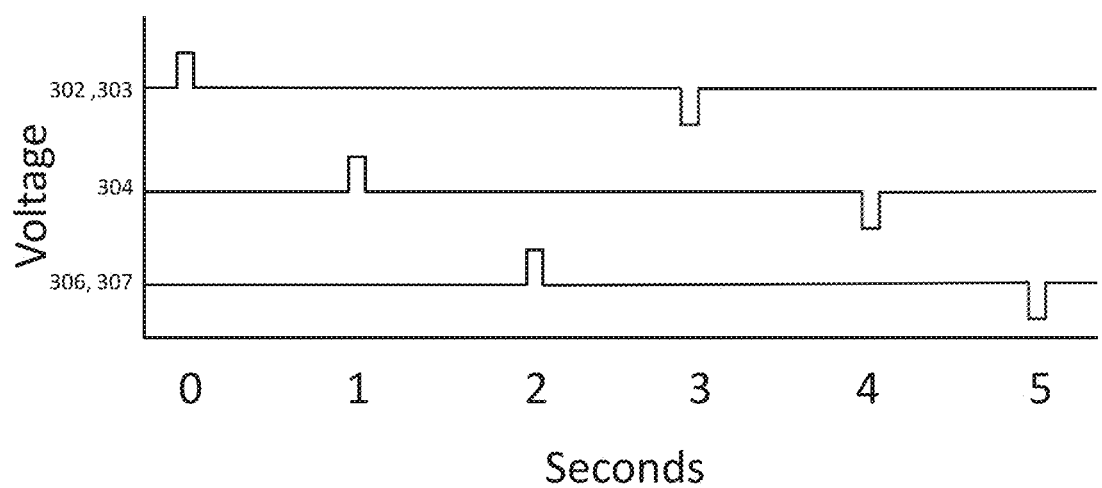
FIG. 4 is an illustrative timing diagram of a variation of a shock wave system.

FIG. 4 is an illustrative timing diagram of a variation of a shock wave system 300 for selectively coupling electrodes to a power source with a selectively delivered direction of current. For example, the controller 310 may activate the different sets of electrode assemblies sequentially (e.g., one at a time) at a first voltage polarity and then activate the different sets of electrode assemblies sequentially at a second voltage polarity. This reserves all of the high voltage for each shock wave source to thus form shock waves of maximum strength to be applied to the calcium deposits all along the vasculature. Reversing the polarity in the subsequent pulse for each of the electrode assemblies 302, 303, 304, 306, and 307 may distribute electrode wear and shock wave strength more evenly within the electrode pairs of the electrode assemblies, thus increasing the longevity and consistency of the shock wave device. In other examples, the voltage polarity of an electrode assembly may vary pulse to pulse, every second pulse, every third pulse, and is not particularly limited. Furthermore, the voltage polarity may vary randomly. For example, for a set of 50 pulses being split evenly between a first voltage polarity (e.g., positive pulse) and a second voltage polarity (e.g., negative pulse), the voltage polarity need not switch every pulse. As an illustrative example, 8 pulses at the first voltage polarity may be followed by 5 pulses at the second voltage polarity, then 7 pulses at the first voltage polarity, 5 pulses at the second voltage polarity, 10 pulses at the first voltage polarity, and 15 pulses at the second voltage polarity. Accordingly, while the total number of pulses is split evenly between the first and second voltage polarities, the number of switches in polarity does not necessarily depend on the current flow ratio.

In some variations, a multiplexer may be coupled to one or more of the electrode assemblies 302, 303, 304, 306, and 307, as depicted in FIG. 3. For example, any of the voltage polarity switching sequences discussed herein may be incorporated with the multiplexer 316. In some variations, the selection of voltage polarity may be independent of the electrode assembly selected by a multiplexer. Alternating polarity and timing may provide the dual benefits of distributing positive pulse wear over multiple electrodes and increasing rest time for the electrode assemblies.

Figure 5:
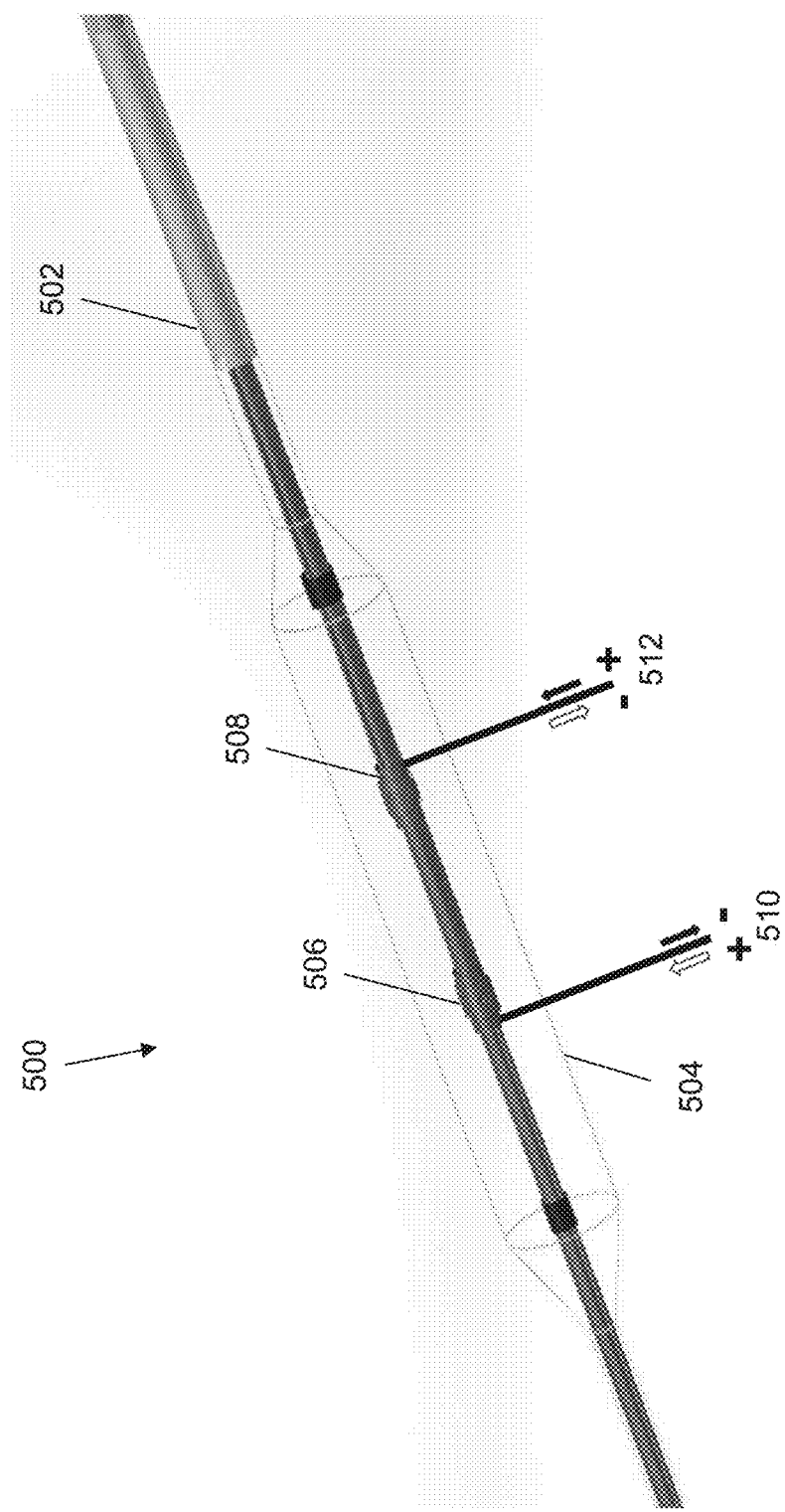
FIG. 5 is a perspective view of another variation of a shock wave device.

The polarity switching and multiplexing described above may be applied to any of the shock wave devices described herein, including the illustrative variations of FIGS. 5-7B as described in detail below. In one variation, a shockwave device having a plurality of electrode assemblies is described. In particular, FIG. 5 depicts the distal portions of a shock wave device having two electrode assemblies 506, 508. In particular, FIG. 5 depicts one variation of a shock wave device 500 comprising an elongate member 502, a first electrode assembly 506 at a first location along the length of the elongate member 502, a second electrode assembly 508 at a second location along the length of the elongate member 502, and optionally, an enclosure 504 configured to be fillable with a conductive fluid to sealably enclose the first and second electrode assemblies 506, 508. In some variations, the enclosure may comprise a membrane and/or a balloon may be made of an electrically insulating material that may be non-compliant (e.g., PET, etc.), semi-compliant (e.g., PBAX, nylon, PEBA, polyethylene, etc.), and/or compliant (e.g., polyurethane, silicone, etc.). The enclosure 504 may enclose any number of electrode assemblies.

The shock wave device 500 may comprise a fluid lumen (not shown) that is in communication with a fluid source that introduces a conductive fluid into the enclosure 506. A voltage source (not shown) having a first terminal 510 and a second terminal 512 may be coupled to the shock wave device 500. As discussed above, the polarity of the terminals 510, 512 may vary per pulse or in a predetermined sequence. An energy pulse may be applied to the electrode pairs 506, 508, thereby generating one or more shock waves that may propagate through the fluid to impinge on a calcified obstruction. Although the shock wave device 500 in FIG. 5 is depicted as having two electrode pairs 506, 508, it should be understood that other variations may have a different number of electrode pairs (e.g., 3, 4, 5, 6 or more electrode pairs).

Figure 6A:
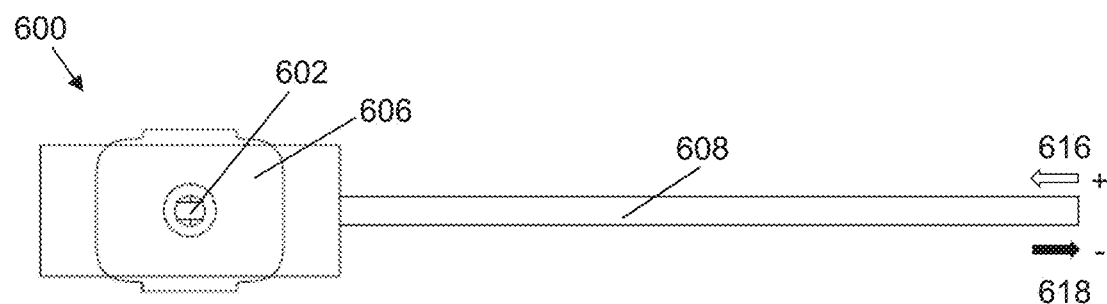
FIGS. 6A-6C are illustrative depictions of another variation of an electrode assembly.
Figure 6B:
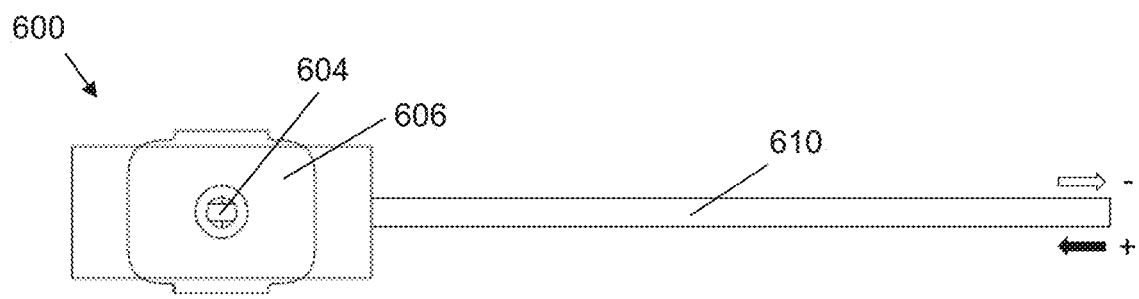

In some variations, the electrode assemblies 506, 508 each may comprise two inner electrodes that are positioned circumferentially opposite each other, an insulating sheath with two openings aligned over the two inner electrodes, and an outer common electrode with two openings that are coaxially aligned with the two openings of the insulating sheath. FIGS. 6A-6C illustrate one variation of an electrode assembly in this configuration including two inner electrodes and an outer common electrode. Each of the electrode assemblies 506, 508 may be configured to generate a pair of directed shock waves, where the shock waves resulting from a high voltage pulse to the first inner electrode propagate in a direction that is opposite to the direction of the shock waves resulting from a high voltage pulse to the second inner electrode. In some variations, the electrode assemblies 506, 508 may generate shock waves that propagate outward from different locations around the circumference of elongate member 502. For example, the electrode assembly 506 may generate shock waves that propagate from the left and right longitudinal side of the elongate member, while the electrode assembly 508 may generate shock waves that propagate from the top and bottom longitudinal side of the elongate member 502.

In other variations, the electrode assembly 506 may generate a pair of shock waves that propagate outward from positions at 0 degrees and 180 degrees around the circumference of the elongate member 502, while the electrode assembly 508 may generate a pair of shock waves that propagate outward from positions at 60 degrees and 240 degrees around the circumference of the elongate member. In still other variations, electrode assemblies 506, 508 may each generate a pair of shock waves that propagate outward at the same locations around the circumference of the elongate member, but from different locations along the length of the elongate member. Optionally, one or more radiopaque marker bands may be provided along the length of the elongate member to allow a practitioner to identify the location and/or orientation of the shock wave device 500 as it is inserted through the vasculature of a patient.

It should be appreciated that shock wave devices with a plurality of electrode assemblies distributed along the length of a catheter may be suitable for use in angioplasty procedures to break up calcified plaques that may be located along a length of a vessel. Shock wave devices with a plurality of electrode assemblies along the length of a curved elongate member may be suitable for use in valvuloplasty procedures to break up calcified plaques that may be located around the circumference of a valve (e.g., at or around the leaflets of a valve). It should be noted that the circuit diagram of FIG. 2A and the simplified layout of FIG. 2B correspond electrically to FIG. 5 embodiment, when the electrode assemblies 506, 508 each include two electrode pairs as shown in FIG. 6.

FIGS. 6A-6B depict top and bottom views, respectively, of one variation of a shock wave device having an electrode assembly 600 that may be configured to generate shock waves in opposite directions. FIG. 6A is a top view of the electrode assembly 600 where the first inner electrode 602 is depicted and FIG. 6B is a bottom view of the electrode assembly 600 where the second inner electrode 604 is depicted. The first and second inner electrodes share a common electrode 606 and are located circumferentially opposite each other (i.e., 180 degrees apart). The first electrode 602 may be connected to a first voltage output terminal V01 of a voltage source of a controller (not shown in FIGS. 6A-6B) by a first wire 608 and the second electrode 604 may be connected to a second voltage output terminal V02 of a voltage source of the controller by a second wire 610. The first electrode 602 and the common electrode 606 form a first electrode pair that may generate a first shock wave that propagates outwards in a first shock wave direction, and the second electrode 604 and the common electrode 606 form a second electrode pair that may generate a second shock wave that propagates outwards in a second shock wave direction that is opposite to the first shock wave direction. For a positive pulse provided in a first current direction 616, current flows from the first electrode pair to the second electrode pair. Likewise, for a negative pulse provided in a second current direction 618 opposite the first current direction 616, current flows from the second electrode pair to the first electrode pair.

A difference in surface area of conductive regions within an electrode pair may be provided to generate larger shock waves. For instance, the surface area of the edges of the first electrode 602 and the second electrode 604 may serve as conductive regions, and may be the portions of the electrodes which are most likely to wear due to high energy pulses. An electrode such as the common electrode 606 may form two conductive regions for each of the first and second electrodes 602, 604 having different surface areas. In some variations, a surface area of a conductive region of the first electrode 602 and second electrode 604 may be smaller in surface area relative to the common electrode 606. Therefore, the longevity of the electrode assembly 600 may depend on the rate of depletion of the smaller electrodes 602, 604.

As energy pulses are applied to the electrodes pairs to form shock waves, erosion of electrode material from the inner and outer electrodes may increase a distance between the electrodes in the electrode pair until a plasma arc is no longer to likely form. At this point, the electrode pair has failed and reached the end of its lifespan. As discussed in further detail below, the degree of erosion and wear may be determined by measuring one or more of voltage drop, voltage pulse width, low voltage analogs of voltage pulse width, and/or any signals that indicate (or are correlated with) the duration of a high-voltage pulse across an electrode pair.

Figure 6C:
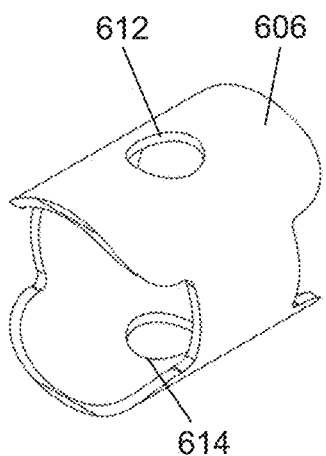

FIG. 6C depicts a perspective view of the outer common electrode 606. As depicted there, first opening 612 may be located directly across from second opening 614. The outer common electrode 606 may have the second opening 614 coaxially aligned over the second inner electrode, and the first inner electrode 604 may be coaxially aligned with the first opening 612 of the outer common electrode 606. This configuration may generate a first shock wave that propagates outwards in a first direction and a second shock wave that propagates outwards in a second direction that is opposite to the first direction.

Turning back to FIGS. 6A and 6B, the wires 608, 610 may be electrically insulated along their length (e.g., by an insulating coating or sheath made of, for example, polyimide, PEBA, PET, FEP, PTFE, etc.) except for one or more regions where the electrically conductive core of the wire is exposed to contact a portion of the inner and/or outer electrode. The wires 608, 610 may be made of any conductive material, for example, free oxygen copper or copper or silver.

Figure 7A:
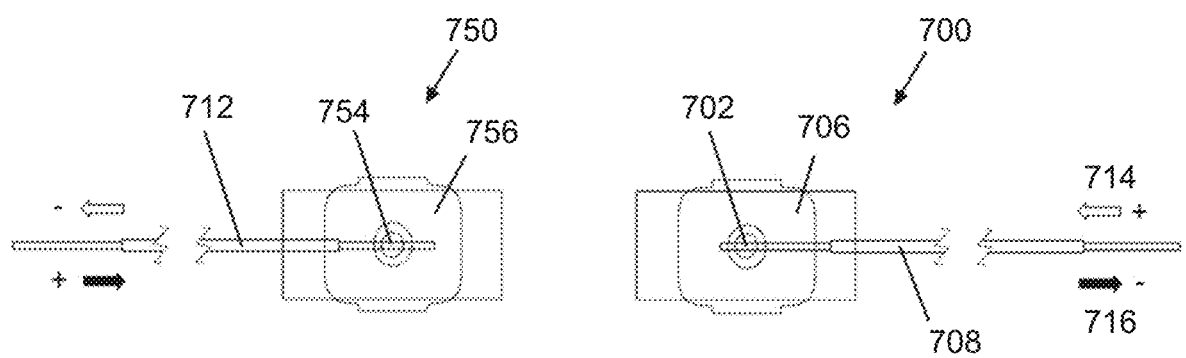
FIGS. 7A-7B are illustrative depictions of a variation of a series of electrode assemblies.
Figure 7B:
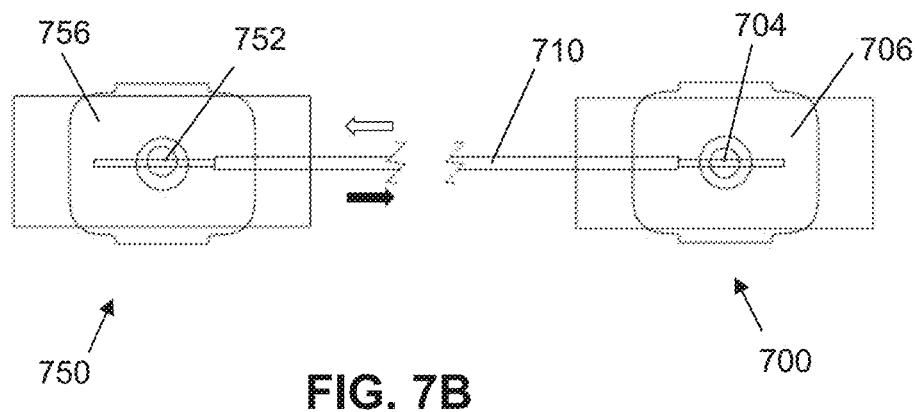

FIGS. 7A-7B depict top and bottom views of one variation of a shock wave device having a first electrode assembly 700 and a second electrode assembly 750 that may be configured to generate shock waves along a length of the shock wave device. The electrode assemblies 700, 750 may be connected in series with respect to each other such that activating a first electrode assembly 700 also activates a second electrode assembly 750. In some variations, it may be desirable to have multiple shock wave sources without as many wires and using fewer terminals on a controller. For example, connecting two electrode assemblies in series may allow the shock wave device to simultaneously generate up to four different shock waves using just two voltage output terminals (e.g., one positive channel and one negative channel). In addition, reducing the number of wires that extend along the length of the elongate member may allow the elongate member to bend and flex more freely as it is advanced through the vasculature of a patient (e.g., may allow for a tighter turning radius).

FIG. 7A is a top view of the electrode assemblies 700, 750 where the first inner electrode 706 and the fourth inner electrode 754 are depicted. FIG. 7B is a bottom view of the electrode assemblies 700, 750 where the second inner electrode 704 and the third inner electrode 752 are depicted. The first and second inner electrodes 702, 704 share a first common electrode 706 and are located circumferentially opposite each other (i.e., 180 degrees apart). The third and fourth inner electrodes 752, 754 share a second common electrode 756 and are also located circumferentially opposite each other. Alternatively, the inner electrodes and electrode assemblies may be offset from each other in some other manner as described above.

The first electrode 702 and the first common electrode 706 form a first electrode pair that may generate a first shock wave that propagates outwards in a first direction, and the second electrode 704 and the first common electrode 706 form a second electrode pair that may generate a second shock wave that propagates outwards in a second direction. Likewise, the third electrode 752 and the second common electrode 756 form a third electrode pair that may generate a third shock wave that propagates outwards in a third direction, and the fourth electrode 754 and the second common electrode 756 form a fourth electrode pair that may generate a fourth shock wave that propagates outwards in a fourth direction.

The first and second electrode assemblies 700, 750 in FIGS. 7A-7B may be connected in series. The first electrode 702 may be connected to a first voltage output terminal V01 of a voltage source of a controller (not shown in FIGS. 7A-7B) by a first wire 708. The second electrode 704 may be connected to the third electrode 752 via a second wire 710 (e.g., an interconnect wire). The fourth electrode 754 may be connected to a second voltage output terminal V02 of the voltage source of the controller by a third wire 712. Therefore, for a positive pulse provided in a first current direction 714, current flows (in ascending order) from the first electrode pair to the fourth electrode pair. Likewise, for a negative pulse provided in a second current direction 716 opposite the first current direction 714, current flows (in descending order) from the fourth electrode pair to the first electrode pair. Each of the first through fourth electrodes 702, 704, 752, 754 may be smaller in size relative to the first and second common electrodes 706, 756. In some variations, size may refer to the total size of the electrode and/or a surface area of a conductive region of the electrode. Therefore, the longevity of the electrode assemblies 700, 750 may depend on the rate of depletion of the smaller electrodes 702, 704, 752, 754.

Any of the shock wave devices described herein may be provided in a shock wave system suitable for use in an angioplasty or valvuloplasty procedure. A shock wave system (not shown) may include a shock wave device, catheter, a high voltage pulse generator (e.g., voltage source), and/or an enclosure configured to be fillable with a conductive fluid. The catheter may have a guide wire lumen therethrough. In some variations, the high voltage pulse generator may be a 0.1 kV to 10 kV pulsed power supply, for example, a 2 kV to 6 kV pulsed supply.

II. Methods

Generally described here are methods for forming shock waves. Any of the shock wave devices described herein may be used in an angioplasty and/or valvuloplasty procedure. The methods described here may include advancing a guide wire from an entry site on a patient (e.g., an artery in the groin area of the leg) to a target region of a vessel (e.g., a region having calcified plaques that need to be broken up. A shock wave device may comprise an axially extending elongate member with a guide wire lumen, an electrode pair comprising a first electrode and a second electrode and/or an electrode assembly provided along a length of the elongate member. The electrode pair and/or electrode assembly may be any of the electrodes described herein.

In some variations, a balloon may be collapsed over the elongate member while the device is advanced through the vasculature. In some variations, the location of the shock wave device may be determined by x-ray imaging and/or fluoroscopy. When the shock wave device reaches the target region, the balloon may be filled with a conductive fluid (e.g., saline and/or saline mixed with an image contrast agent). A series of pulses may be delivered to the first electrode pair and/or electrode assembly to create shock waves that may break up calcified plaque, for example.

In some variations, current flows through the electrode pair and/or electrode assembly in a first direction for some of the pulses in the series and in a second direction that is opposite the first direction for the remaining pulses in the series. In one variation, a first direction of current flow may be provided for at least one of the pulses. In another variation, a first direction of current flow may be provided for at least about 5% of the pulses. In another variation, a first direction of current flow may be provided for at least about 10% of the pulses. In another variation, a first direction of current flow may be provided for at least about 15% of the pulses. In another variation, a first direction of current flow may be provided for at least about 20% of the pulses. In another variation, a first direction of current flow may be provided for at least about 25% of the pulses. In another variation, a first direction of current flow may be provided for at least about 30% of the pulses. In yet another variation, a first direction of current flow may be provided for at least about a third of the pulses. In another variation, a first direction of current flow may be provided for at least about 40% of the pulses. In another variation, a first direction of current flow may be provided for at least about 45% of the pulses. In still another variation, a first direction of current flow may be provided for at least about half of the pulses.

In still other variations, the ratio of current flow of the pulses in the first direction to the second direction may be about 1:6. In another variation, the ratio of current flow of the pulses in the first direction to the second direction may be about 5:6. In another variation, the ratio of current flow of the pulses in the first direction to the second direction may be about 1:8. In another variation, the ratio of current flow of the pulses in the first direction to the second direction may be about 3:8. In another variation, the ratio of current flow of the pulses in the first direction to the second direction may be about 5:8. In another variation, the ratio of current flow of the pulses in the first direction to the second direction may be about 7:8. In another variation, the ratio of current flow of the pulses in the first direction to the second direction may be about 1:9. In another variation, the ratio of current flow of the pulses in the first direction to the second direction may be about 2:9. In another variation, the ratio of current flow of the pulses in the first direction to the second direction may be about 4:9. In another variation, the ratio of current flow of the pulses in the first direction to the second direction may be about 5:9. In another variation, the ratio of current flow of the pulses in the first direction to the second direction may be about 7:9. In another variation, the ratio of current flow of the pulses in the first direction to the second direction may be about 8:9. In another variation, the ratio of current flow of the pulses in the first direction to the second direction may be about 1:12. In another variation, the ratio of current flow of the pulses in the first direction to the second direction may be about 1:16. In another variation, the ratio of current flow of the pulses in the first direction to the second direction may be about 1:32. The number of pulses in each direction of current flow (e.g., ratio of current flow of first direction to second direction) may be determined based on a desired longevity of the shock wave device, shock wave uniformity, shock wave energy, and so forth.

The number of transitions of current flow directions is not particularly limited. In some instances, the direction of current flow may be switched according to the ratio of pulses in the first direction to the second direction. In other instances, the direction of current flow may vary randomly for each pulse so long as the total number of pulses maintains a predetermined ratio of current flow direction. Accordingly, the current flow direction need not switch for every pulse even if the number of pulses in each direction is equal. Alternating on average the direction of current flow of the pulses may about double the durability of the smaller electrodes, and thus the lifetime of the electrode assembly. Even when the electrodes in an electrode pair are of equal size, alternating the direction of current flow so that each electrode receives about the same number of positive pulses will distribute the wear over two electrodes so as to about double the electrode pair durability.

Furthermore, shock waves output from different electrode pairs may have more uniform strength on average as polarity switching allows each electrode pair to receive the positive pulse. This allows more predictable shock waves with less variance in shock wave strength.

The progress of the plaque break-up may be monitored by x-ray and/or fluoroscopy. The shockwave device may be moved along the length of the vessel if the calcified region is longer than the length of the elongate member with the electrode assemblies, and/or if the calcified region is too far away from the electrode assemblies to receive the full force of the generated shock waves. For example, the shockwave device may be stepped along the length of a calcified vessel region to sequentially break up the plaque.

Voltage and current measurements may be taken at the load (in this case, the electrode assembly) to determine the condition of the shock wave device as the pulses are delivered. As discussed in further detail below, measurements including voltage drop, voltage pulse width, and current flow may be used to determine a condition/longevity of the shock wave device.

In some variations, polarity switching of the pulses may be based on the condition of the electrodes in a shock wave device. For example, the direction of current flow of pulses in a series may be determined using measurements correlated to voltage drop, such as voltage pulse width, which may be correlated to the condition of the electrodes. For instance, a first voltage pulse width across the electrode pair may be measured for a first direction of current flow and a second voltage pulse width across the electrode pair may be measured for a second direction of current flow. A difference (if any) between the first voltage pulse width and the second voltage pulse width may indicate a difference in electrode wear. In some cases, differences in the degree of electrode erosion between the electrodes in a pair may lead to a shorter lifespan of the overall shock wave device. By switching the direction of current flow based on the measured voltage pulse widths to balance the wear between the first and second electrodes, the lifetime of a shock wave device may be prolonged.

In some variations, the direction of current flow for pulses in a series (e.g., the polarity of each of the voltage pulses in a series) may be selected according to the measured voltage pulse widths. For instance, the direction of current flow may be selected such that a difference between the voltage pulse width across the electrode pair when the current flows in a first direction and the voltage pulse width when the current flows in a second direction are within a predetermined threshold. In other variations, the direction of current flow may be selected such that the voltage pulse width across the electrode pair when the current flows in a first direction is substantially equal to the voltage pulse width across the electrode pair when the current flows in a second direction. The ratio of current flow of the pulses in a first direction to a second (opposite) direction (i.e., polarity ratio) may be determined at least in part by the measured voltage pulse width. For example, if the measured voltage pulse width in the first direction of current flow (i.e., first polarity) meets or exceeds a predetermined threshold, the controller may determine that the first electrode of the electrode pair has a greater degree of erosion than the second electrode of the electrode pair. The controller may then adjust the polarity ratio so that the second direction of current flow (i.e., second polarity) is increased relative to the first direction of current flow. This may help reduce or stabilize the erosion rate of the first electrode so that the overall electrode pair may be more durable (e.g., longer lifespan) as compared to a shock wave system where the polarity is not switched and/or polarity ratio is not adjusted.

The electrode assemblies of the shock wave device may be connected in series, and may be activated simultaneously and/or sequentially, as described above. For example, a pair of electrode assemblies may be connected in series and activated simultaneously or sequentially.

Once the calcified region has been sufficiently treated, the balloon may be inflated further or deflated, and the shock wave device and guide wire may be withdrawn from the patient. Wear of the shock wave device may be evaluated through visual inspection by microscopy.

III. Examples

In the following examples, test results are provided for electrodes to compare electrical energy delivery to a set of electrodes receiving using a constant polarity (static device) for every pulse and alternating polarity as described above (switching device). Electrical current, voltage, energy measurements, and visual inspection as a function of pulses were taken of an 8 gap copper coil emitter to determine erosion, electrode integrity, and electrode lifetime.

After pulsing the devices, bright field microscopy evaluation was performed to visually inspect the wear of the electrodes. It was determined that the positive terminals in the static device had more consumed conductor than the negative terminals. The switching device had more even wear than the static device. In FIGS. 8 and 9A-9B discussed below, the shock wave devices were pulsed at 0.5 Hz or slower with a pulse width of about 6 μs.

Figure 8A:
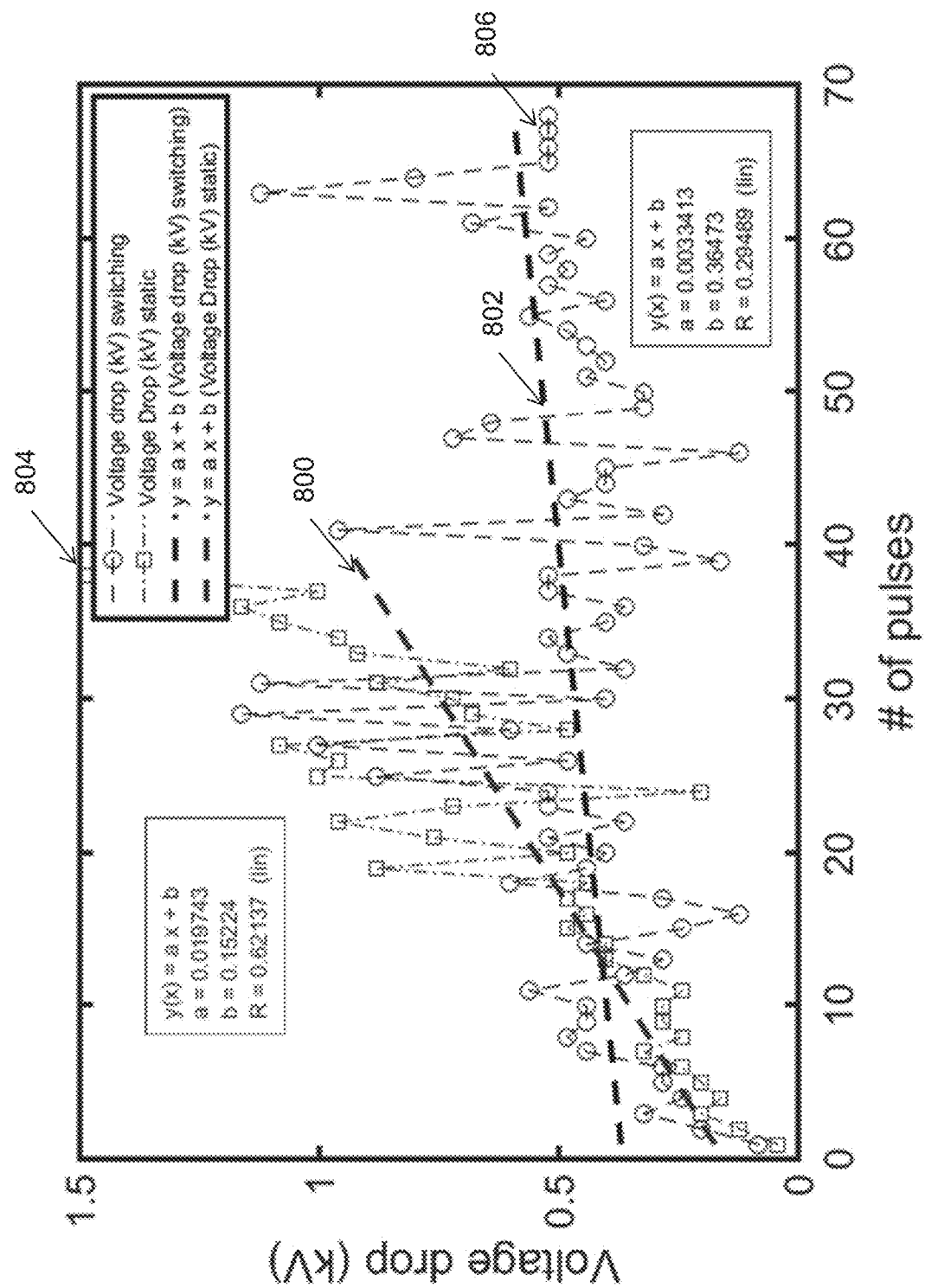
FIG. 8A is an illustrative graph comparing the voltage drop as a function of pulse number between switching and non-switching energy pulses.

FIG. 8A is an illustrative graph of voltage drop (kV) as a function of pulse number. Voltage drop is defined as the difference between the highest and lowest voltage prior to current flow (representing voltage losses which are correlated to electrode wear). As shown in FIG. 8A, voltage drop increases as a function of pulse number. However, static energy delivery has a much larger rate of voltage drop compared to switching energy delivery indicating more electrode wear. FIG. 8A illustrates the rate of voltage drop (slope a) having a linear best fit (R). From the linear best fits, the voltage losses represented by the voltage drop (kV) increase at a much faster rate 800 for static energy compared to the rate 802 for switching energy. It should be noted that the static shock wave device fails 804 at about 40 pulses before the switching shock wave device fails at about 70 pulses.

Figure 8C:
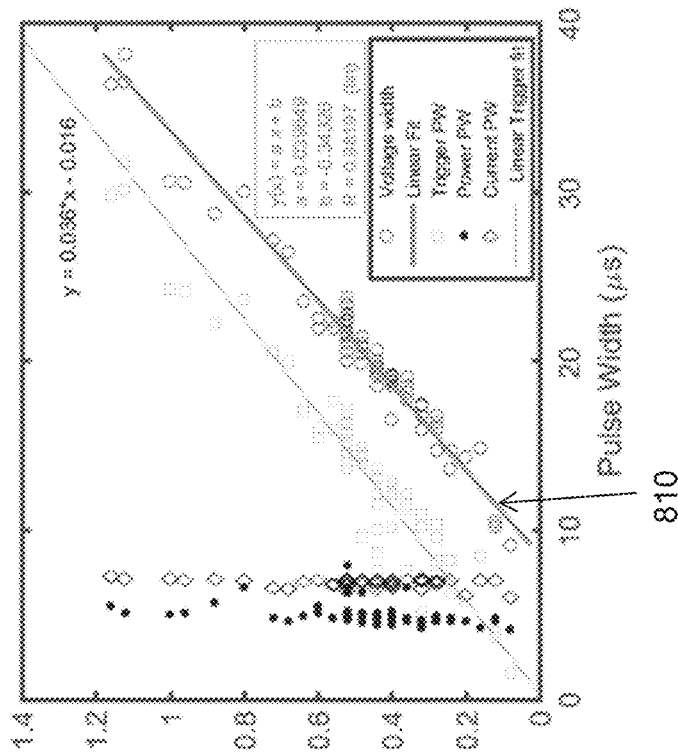
FIGS. 8B and 8C are illustrative graphs comparing voltage drop as a function of pulse width for a non-switching electrode assembly and a switching electrode assembly, respectively.
Figure 8B:
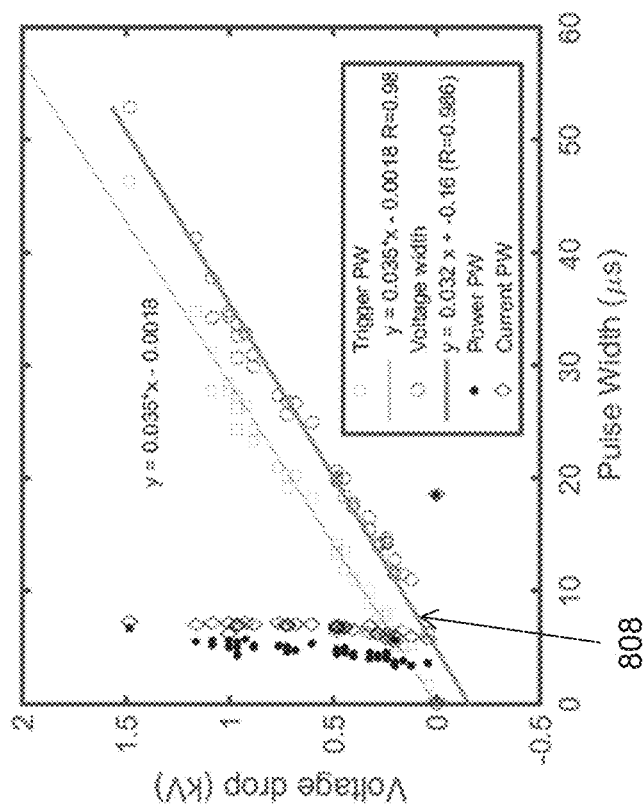

Although voltage drop is plotted in FIG. 8A, voltage pulse width correlates strongly with voltage drop such that measurements of voltage pulse width may be used to monitor the lifetime and/or condition of a shock wave device from pulse to pulse. For example, FIGS. 8B and 8C are illustrative graphs comparing voltage drop as a function of pulse width for a non-switching electrode assembly and a switching electrode assembly, respectively. In FIG. 8B, line 808 represents the high correlation fit between voltage drop and pulse width for a non-switching shock wave device. Similarly, line 810 illustrates a high correlation fit between voltage drop and pulse width for a polarity switching shock wave device. The width of each pulse (e.g., voltage, current) is defined herein as the first time and the last time the pulse reaches 20% of the maximum voltage peak value. Similar to voltage drop (kV), the voltage pulse width increases as a function of pulse number and is an indicator of electrode degradation. In other words, measurement of voltage pulse width may be used as a proxy for voltage drop to monitor the condition (e.g., degradation) of an electrode pair. That is, the longer the measured voltage pulse width, the more the electrode with the positive polarity has eroded or degraded. Alternatively, measurement of an internal signal that indicates the onset and offset of a high voltage pulse across an electrode pair may be used to monitor the condition of the electrodes. For example, the internal signal may be a trigger TTL output signal of the high voltage pulse generator.

FIG. 9A is an illustrative graph of pulse number as a function of voltage polarity. As discussed above, FIG. 9B is an illustrative graph of energy delivered as a function of pulse number. Since more pulses may be provided to a switching device than a static device, the lifetime of the switching device may be about double that of the static device. In FIG. 9B, it is apparent that the number of pulses and the average amount of energy delivered by the switching device is significantly more than the static device due to polarity switching. For instance, the static device provides about 40 pulses before static device failure 900 while the switching device provides about 70 pulses before switching device failure 902.

The test results indicate that switching current flow direction may increase the lifetime and energy delivered of an 8 gap shock wave device over a constant current flow direction 8 gap shock wave device. Visual inspection also shows biased wear of the electrodes when a single direction of current flow is applied compared to alternating current flow. Experimental testing has shown that the voltage pulse width is directly proportional to energy voltage drop prior to current flow. Therefore, a static device has more voltage loss compared to a switching device. The voltage pulse width may be used as a metrology tool to monitor the lifetime and/or condition of a shock wave device from pulse to pulse. Thus, switching the direction of current flow may improve the efficiency and/or consistency of shock waves output by a shock wave device.

It will be understood that the foregoing is only illustrative of the principles of the invention, and that various modifications, alterations and combinations can be made by those skilled in the art without departing from the scope and spirit of the invention. Any of the variations of the various shock wave devices disclosed herein can include features described by any other shock wave devices or combination of devices disclosed. Accordingly, it is not intended that the invention be limited, except as by the appended claims. For all of the variations described above, the steps of the methods need not be performed sequentially.

We claim:

1. A shock wave device comprising: an axially extending elongate member configured to be advanced through a blood vessel to treat a calcified lesion; a first electrode assembly comprising a first electrode pair and a second electrode pair, wherein the first electrode assembly is carried by the elongate member and positioned within a conductive fluid; and a controller coupled to the first electrode assembly, wherein the controller is configured to deliver a series of individual voltage pulses to the first electrode assembly such that each of the voltage pulses creates a shock wave in the conductive fluid to treat the calcified lesion, wherein the controller includes a voltage source having a constant polarity followed by a voltage polarity switch for switching the polarity of the voltage source and causing current to flow through the first electrode assembly in a first direction for some of the pulses in the series and in a second direction opposite the first direction for the remaining pulses in the series and wherein the voltage polarity switch only operates between the delivery of individual voltage pulses so each voltage pulse delivered to the first electrode assembly has a single direction of current flow wherein a first electrode in each of the first and second electrode pairs is coupled to the voltage polarity switch and wherein the second electrode in the first electrode pair is coupled to the second electrode of the second electrode pair and wherein the first electrode in each of the first and second electrode pairs has a surface area smaller than a surface area of the associated second electrode in the first and second electrode pairs.

2. The device of claim 1 wherein the voltage polarity switch causes the current to flow in the second direction for between twenty five percent and fifty percent of the pulses in the series.

3. The device of claim 1 wherein a first wire connects the first electrode of the first electrode pair to a first terminal of the voltage polarity switch, and a second wire connects the first electrode of the second electrode pair to a second terminal of the voltage polarity switch.

4. The device of claim 1 further comprising a second electrode assembly coupled in series to the first electrode assembly, the second electrode assembly including a third electrode pair and a fourth electrode pair.

5. The device of claim 4 wherein a first electrode in the third electrode pair is connected to the first electrode of the second electrode pair, and a first electrode in the fourth electrode pair is coupled to the voltage polarity switch and wherein the second electrode of the third electrode pair is coupled to the second electrode of the fourth electrode pair and wherein the first electrode in each of the third and fourth electrode pairs has a surface area smaller than a surface area of the associated second electrodes in the third and fourth electrode pairs.

6. The device of claim 5 wherein a first wire connects the first electrode of the first electrode pair to a first terminal of the voltage polarity switch, a second wire connects the first electrode of the second electrode pair to the first electrode of the third electrode pair, and a third wire connects the first electrode of the fourth electrode pair to a second terminal of the voltage polarity switch.

7. The device of claim 1 further comprising a second electrode assembly, wherein the controller comprises a multiplexer configured to selectively deliver the series of pulses to the first electrode assembly and the second electrode assembly.

8. The device of claim 1 further comprising a fluid enclosure surrounding the first electrode assembly.

9. The device of claim 8 wherein the fluid enclosure comprises a balloon surrounding a portion of the elongate member, wherein the balloon is configured to be filled with the conductive fluid, and wherein the first electrode assembly is enclosed within and spaced from the balloon.

* * * * *